US010709860B2

(12) United States Patent
Matula, Jr. et al.

(10) Patent No.: US 10,709,860 B2
(45) Date of Patent: Jul. 14, 2020

(54) PATIENT INTERFACE WITH AN ADJUSTABLE CUSHION

(71) Applicant: RIC INVESTMENTS LLC, Wilmington, DE (US)

(72) Inventors: Jerome Matula, Jr., Monroeville, PA (US); Jason P. Eaton, Hunker, PA (US); Peter Chi Fai Ho, Pittsburgh, PA (US); James DiPasquale, Allison Park, PA (US); Derrick Andrews, Markleton, PA (US); Eugene N. Scarberry, Trafford, PA (US); Steven C. Stegman, Gibsonia, PA (US)

(73) Assignee: RIC Investments LLC, Wilmington, DE (US)

( * ) Notice: Subject to any disclaimer, the term of this patent is extended or adjusted under 35 U.S.C. 154(b) by 1018 days.

(21) Appl. No.: 14/936,114

(22) Filed: Nov. 9, 2015

(65) Prior Publication Data
US 2016/0129210 A1 May 12, 2016

Related U.S. Application Data

(60) Division of application No. 14/076,509, filed on Nov. 11, 2013, now abandoned, which is a continuation of
(Continued)

(51) Int. Cl.
*A61M 16/06* (2006.01)
*A61M 16/08* (2006.01)

(52) U.S. Cl.
CPC ........ *A61M 16/0622* (2014.02); *A61M 16/06* (2013.01); *A61M 16/065* (2014.02);
(Continued)

(58) Field of Classification Search
CPC ........ A61M 16/00; A61M 16/06–0655; A61M 16/065; A61M 16/0661; A61M 16/0683;
(Continued)

(56) References Cited

U.S. PATENT DOCUMENTS

| 4,526,196 A | 7/1985 | Pistillo |
| 4,782,854 A | 11/1988 | Rozek |

(Continued)

FOREIGN PATENT DOCUMENTS

| WO | WO2004012803 A1 | 2/2004 |
| WO | WO2004071565 A1 | 8/2004 |

OTHER PUBLICATIONS

Puritan Bennett, "Wake Up to new Sleep Products", product brochure, 2004.
PCT Search Report and Written Opinion, dated Sep. 18, 2007.

*Primary Examiner* — Rachel T Sippel
(74) *Attorney, Agent, or Firm* — Michael W. Haas

(57) ABSTRACT

A patient interface of the present invention includes a faceplate including a plurality of headgear attachment elements, a seal member operatively coupled to the faceplate; and an adjustment mechanism coupling the seal member to the faceplate. The adjustment mechanism controls the position of the seal member relative to the faceplate such that the seal member is moveable from a first position to a second position and is maintained in the second position during use of the patient interface after being moved to the second position.

12 Claims, 36 Drawing Sheets

Related U.S. Application Data application No. 13/406,025, filed on Feb. 27, 2012, now Pat. No. 8,596,275, which is a continuation of application No. 11/500,014, filed on Aug. 7, 2006, now Pat. No. 8,245,711.

(60) Provisional application No. 60/708,319, filed on Aug. 15, 2005.

(52) U.S. Cl.
CPC .... *A61M 16/0605* (2014.02); *A61M 16/0611* (2014.02); *A61M 16/0616* (2014.02); *A61M 16/0638* (2014.02); *A61M 16/0644* (2014.02); *A61M 16/0655* (2014.02); *A61M 16/0816* (2013.01); *A61M 16/0683* (2013.01)

(58) Field of Classification Search
CPC ........... A61M 16/0638; A62B 7/00–14; A62B 18/00; A62B 18/06; A62B 18/08; A62B 18/084; A62B 18/02–025
See application file for complete search history.

(56) References Cited

U.S. PATENT DOCUMENTS

| | | |
|---|---|---|
| 4,971,051 A | 11/1990 | Toffolon |
| 5,074,297 A | 12/1991 | Venegas |
| 5,662,101 A | 9/1997 | Ogden |
| 5,941,245 A | 8/1999 | Hannah |
| 6,530,373 B1 | 3/2003 | Patron |
| 6,543,445 B1 | 4/2003 | Hopper |
| 6,805,117 B1 | 10/2004 | Ho |
| 6,851,425 B2 | 2/2005 | Jaffre |
| 6,860,268 B2 | 3/2005 | Bohn |
| 7,047,972 B2 | 5/2006 | Ging |
| 7,069,932 B2 | 7/2006 | Eaton |
| 7,455,063 B2 | 11/2008 | Geiselhart |
| 7,490,608 B2 | 2/2009 | Brown |
| 7,600,514 B2 | 10/2009 | Woodard |
| 7,827,990 B1 * | 11/2010 | Melidis ................ A61M 16/06 128/206.24 |
| 2002/0023649 A1 | 2/2002 | Gunaratnam |
| 2004/0003816 A1 | 1/2004 | Cannon |
| 2004/0025883 A1 | 2/2004 | Eaton |
| 2004/0099272 A1 | 5/2004 | Kwok |
| 2004/0182398 A1 * | 9/2004 | Sprinkle ............... A61M 16/06 128/207.13 |
| 2004/0216747 A1 | 11/2004 | Jones, Jr. |
| 2005/0011522 A1 | 1/2005 | Ho |
| 2005/0076913 A1 | 4/2005 | Ho |
| 2005/0150497 A1 | 7/2005 | Eifler |
| 2005/0150499 A1 | 7/2005 | Bordewick |
| 2005/0155603 A1 | 7/2005 | Frerichs |
| 2005/0268914 A1 | 12/2005 | Paoluccio |
| 2006/0118119 A1 | 6/2006 | Berthon-Jones |
| 2006/0130844 A1 | 6/2006 | Ho |
| 2006/0144405 A1 | 7/2006 | Gunaratnam |
| 2007/0175480 A1 | 8/2007 | Gradon |
| 2007/0215161 A1 | 9/2007 | Frater |

* cited by examiner

PATIENT INTERFACE WITH AN ADJUSTABLE CUSHION

CROSS-REFERENCE TO RELATED APPLICATIONS

This application is a Divisional of U.S. patent application Ser. No. 14/076,509, filed Nov. 11, 2013, which is a Continuation of U.S. patent application Ser. No. 13/406,025, filed Feb. 27, 2012, which is a Continuation of U.S. patent application Ser. No. 11/500,014, filed Aug. 7, 2006, now U.S. Pat. No. 8,245,711, granted Aug. 21, 2012, which claims priority under 35 U.S.C. § 119(e) from provisional U.S. patent application No. 60/708,319 filed Aug. 15, 2005, the contents of which are incorporated herein by reference.

BACKGROUND OF THE INVENTION

1. Field of the Invention

The present invention pertains to a patient interface for use in a non-invasive pressure support or ventilation system that supplies a flow of gas to the airway of a patient, and, in particular, to a patient interface having a seal member that is selectively adjustable relative to a faceplate or other seal supporting structure so that the user can control the position of the seal to optimize comfort and fit while also minimizing gas leak.

2. Description of the Related Art

There are numerous situations where it is necessary or desirable to deliver a flow of gas non-invasively to the airway of a patient, i.e., without intubating the patient or surgically inserting a tracheal tube in the esophagus. For example, it is known to ventilate a patient using a technique known as non-invasive ventilation (NIV). It is also known to deliver a pressure support therapy to treat a medical disorder, such as sleep apnea syndrome, in particular, obstructive sleep apnea (OSA), cheynes-stokes respiration, and congestive heart failure. Typical pressure support therapies include providing a continuous positive airway pressure (CPAP) or a variable airway pressure to the airway of the patient. Examples of variable airway pressure therapies include providing a bi-level pressure that varies with the patient's respiratory cycle, a proportional pressure that varies the delivered pressure based on the patient's respiratory effort or flow, and an auto-titrating pressure that varies the delivered pressure based on the monitored condition of the patient.

Non-invasive ventilation and pressure support therapies involve the placement of a patient interface, which is typically a nasal or nasal/oral mask, on the face of a patient to interface the ventilator or pressure support system with the airway of the patient so that a flow of gas can be delivered from the pressure/flow generating device to the airway of the patient. Typically patient interfaces include a mask shell having a cushion attached to the shell that contacts the surface of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Because such masks are typically worn for an extended period of time, a variety of concerns must be taken into consideration. For example, in providing CPAP to treat OSA, the patient normally wears the patient interface all night long while he or she sleeps. One concern in such a situation is that the patient interface is as comfortable as possible, otherwise the patient may avoid wearing the interface device, defeating the purpose of the prescribed pressure support therapy. It is also important that the interface device provides a tight enough seal against a patient's face without discomfort so that gas leakage from the system at the patient-seal interface is minimized. A dilemma arises in that in order for the mask to maintain a seal without any undue gas leaks around the periphery of the mask, the mask may be compressed against the patient's face, which may decrease comfort.

Many patient interfaces have been develop that attempt to balance the competing interests of patient comfort versus minimizing leakage. In addressing this issue, many patient interfaces have focused on the design of the cushion. Early cushion designs were typically a flap of material or a balloon, i.e., air-filled cushion, that contacted the face of the user. Further design developments including contouring the patient contacting portion of the cushion and/or making the seal customizable to the surface or underlying tissues of the user. Still further cushions have employed multiple flaps so that the outermost flap provides a sealing function. See, e.g., U.S. Pat. No. 4,971,051 to Toffolon.

In addition, U.S. Pat. No. 6,530,373 ("the '373 patent") discloses a patient interface in which the position of the seal relative to the conduit is adjustable over discrete positions. This is done in the '373 patent because there is little or no control of the position of the conduit relative to the patient's face. Allowing the seal position to be adjusted allows the seal to set to a proper angle on the user depending on the position of the conduit. This patient interface, however, does not provide a stable platform on which the seal is mounted.

Although these conventional patient interfaces have advanced the art, the need still exists for a patient interface that improves upon existing devices, for example, to maximize patient comfort while minimizing leak, during delivery of a positive airway pressure or flow of gas to the airway of the user. In addition, existing patient interfaces also may not provide a stable platform that supports the cushion on the patient's face.

SUMMARY OF THE INVENTION

Accordingly, it is an object of the present invention to provide a patient interface that overcomes the shortcomings of conventional patient interfaces. This object is achieved according to one embodiment of the present invention by providing a patient interface that includes a faceplate that includes a plurality of headgear attachment elements, a seal member operatively coupled to the faceplate, and an adjustment mechanism that couples the seal member to the faceplate. The seal member is adjustable relative to the faceplate from a first position to a second position and is maintained in the second position by the adjustment mechanism during use of the patient interface. The adjustment mechanism provides either a plurality of discrete positions for the seal member relative to the faceplate or a potentially infinite number of adjustment positions between these components.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
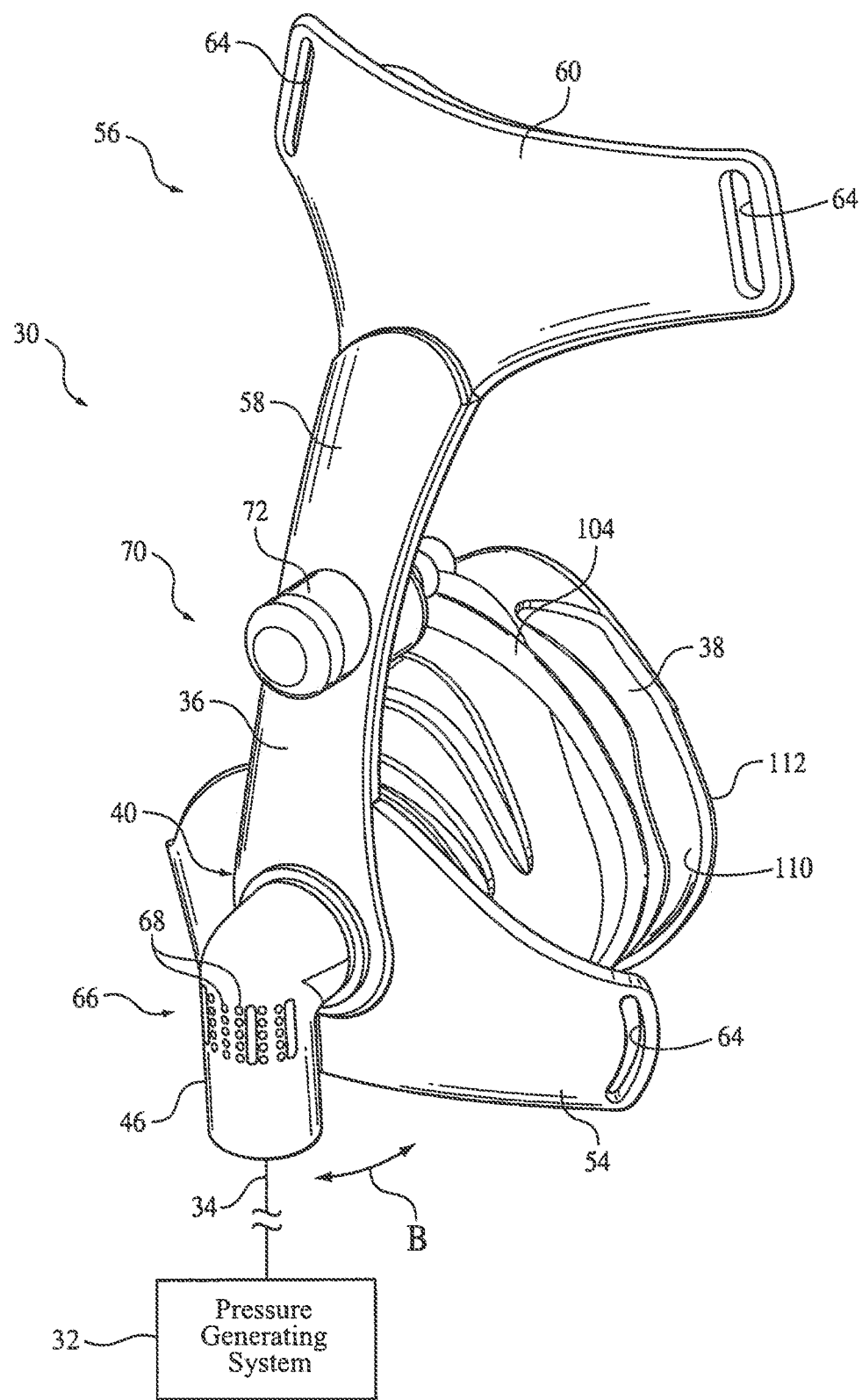
FIG. 1 is a front perspective view of a first embodiment of a patient interface according to the principles of the present invention shown schematically connected to a pressure support system.
Figure 2:
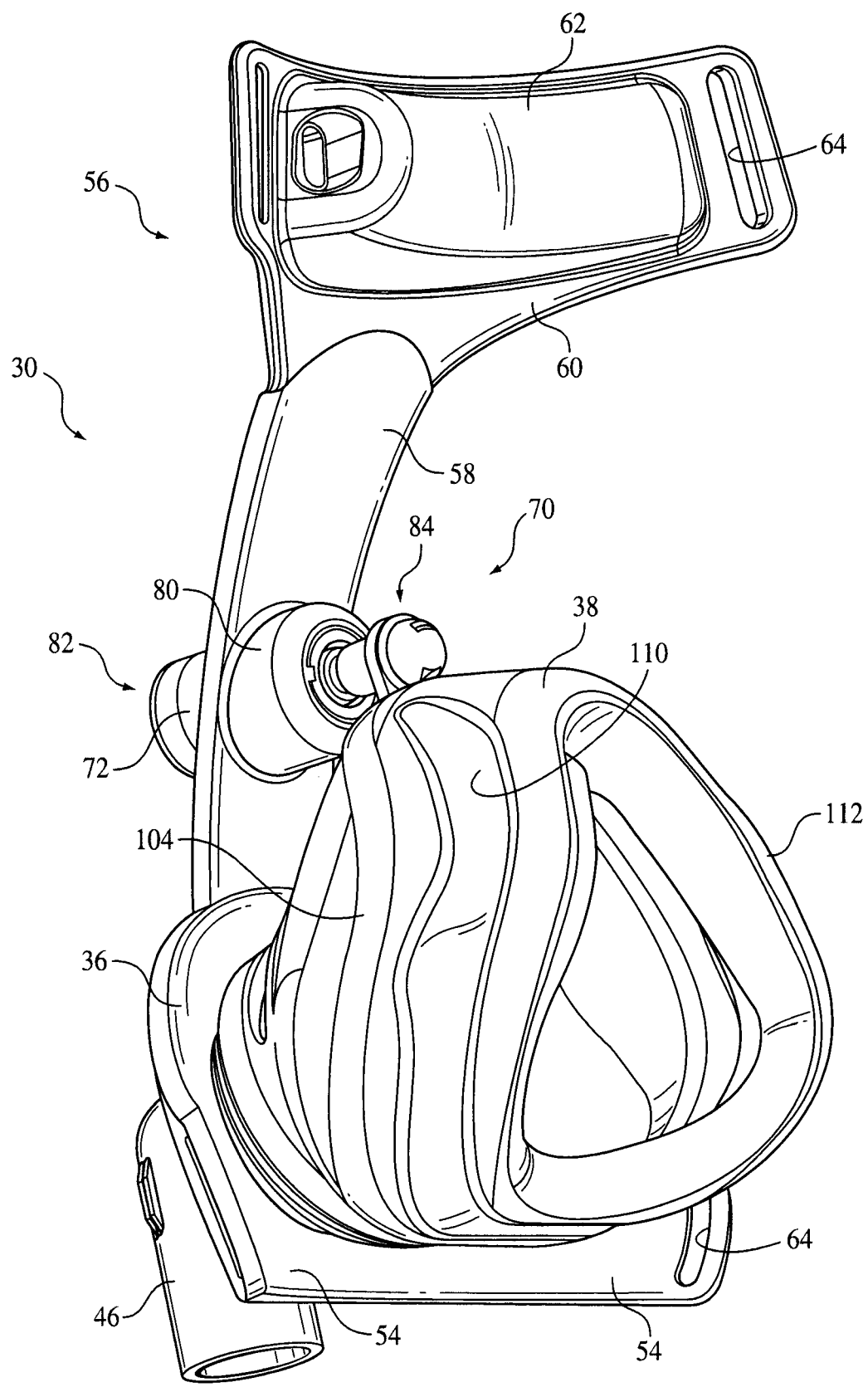
FIG. 2 is a rear perspective view of the patient interface of FIG. 1.

FIGS. 1-6 illustrate a first embodiment of a patient interface 30 according to the principles of the present invention. Patient interface 30 is shown schematically connected to a pressure/flow generating system 32 via a patient circuit 34, which communicates gas from the pressure support system to the patient interface. Pressure/flow generating system 32 is any conventional ventilator or pressure support system. Patient circuit 34 is typically a flexible hose or tube that communicates an output of the pressure/flow generating system with the patient interface. It is to be understood that other accessories used in pressure/flow generating systems, such as a humidifier, pressure sensor, flow sensor, temperature sensor, humidity sensor, bacteria filter, etc. can be used in conjunction with the patient interface of the present invention.

Examples of pressure support systems include, but are not limited to: a ventilator, continuous positive airway pressure (CPAP) device, or a variable pressure device, e.g. an auto-titrating device, proportional assist ventilation (PAV®) device, proportional positive airway pressure (PPAP®) device, C-Flex™ device, Bi-Flex device, or a BiPAP® device manufactured and distributed by Respironics, Inc. of Pittsburgh, Pa., in which the pressure provided to the patient varies with the patient's respiratory cycle so that a higher pressure is delivered during inspiration than during expiration, or other pressure support device. Auto-titrating devices vary the pressure delivered to the patient based on the monitored condition of the patient. C-Flex and Bi-Flex devices vary the pressure based on the flow in the pressure support system or at the airway of the patient, and a PAV device varies the pressure based on the patient's respiratory effort. It is to be understood that the present invention contemplates using any pressure support system with the patient interface of the present invention.

Patient interface 30 includes a faceplate 36 and a seal member 38, which is also referred to as a cushion or seal, coupled to the faceplate. In an exemplary embodiment of the present invention, faceplate 36 is a substantially rigid member that serves as a stable platform on which the seal member is mounted. The present invention also contemplates that the faceplate can be flexible, or have flexible portions to maximize the fit and comfort of the patient interface device on the user. The stability of the faceplate as a support structure for the seal member is accomplished due to the fact that the faceplate itself is secured to the user by means of a headgear assembly (not shown) coupled directly to the faceplate. It can be appreciated that any suitable headgear assembly can be used to secure the patient interface on the user, and that the headgear straps can be attached to the patient interface in any suitable fashion. The details of one technique for attaching the headgear straps to the faceplate are discussed below with reference to FIGS. 7-14.

Referring again to FIGS. 1-6, faceplate 36 includes a seal support portion, generally indicated at 40, to which seal member 38 is mounted. An orifice 42 is provided in seal support portion 40 of faceplate 36 to enable a flow of gas from patient circuit 34 to be communicated to a chamber 44 defined by the seal member of the patient interface. Gas is also communicated in the opposite direction, i.e., from the interior of the patient interface to the patient circuit, through orifice 42. The flow of gas between the seal member and the patient circuit is illustrated by arrow A in FIG. 4.

A coupling member 46, which in the illustrated embodiment is an elbow piece, connects the patient circuit to the interface device via orifice 42. Of course, the present invention also contemplates eliminating coupling member 46 and coupling the patient circuit directly to the faceplate. Coupling member 46 includes a pair of prongs 48 that define a channel 50 to receive the wall of the faceplate and the end of seal member 38. In an exemplary embodiment, the end of seal member 38 is joined to a ring 52 that is more rigid than the end of the seal member to provide a strong, stable mechanical coupling of the seal member to the faceplate. It is to be understood that ring 52 can be eliminated. This configuration allows coupling member 46 to rotate relative to faceplate 36, as indicated by arrow B in FIG. 1. It is to be further understood that other techniques for securing the coupling member to the faceplate are contemplated by the present invention.

Faceplate 36 includes lateral portions 54 and a forehead support, generally indicated at 56. The forehead support includes a forehead arm 58, a forehead pad support 60, and a forehead pad 62. Lateral portions 54 are disposed over the user's cheeks when the patient interface is donned by the user and forehead support extends along the bridge of the nose up to the user's forehead. The entire faceplate can be formed as a unitary structure, or may be formed as separate elements that are connected together in either a fixed relation or in an adjustable relation. For example, the present invention contemplates that the forehead arm can be coupled to the lateral portions such that the forehead arm is rotatable relative to the lateral portions. Lateral portions 54 and forehead pad support 60 include headgear attachment elements to which a headgear strap is attached. In the illustrated embodiment, the headgear attachment members are in the form of a slot 64 defined in the various portions of the faceplate. These slots receive the straps of the headgear as known in the art. As noted above, the headgear attachment elements can have any conventional configuration for attaching a headgear strap to the faceplate.

In the illustrated exemplary embodiment of forehead support 56, forehead pad support 60 is coupled to forehead arm 58, and, in particular, is integral therewith. The present invention also contemplates adjustably coupling the forehead arm to the remainder of the faceplate, such as the portion including lateral portions 54, so that the position of the forehead pad support relative to the lateral portions of the faceplate can be adjusted enabling the patient interface to fit a wide variety of differently sized faces. An example of an forehead support assembly that allows adjustment of the forehead arm and/or the forehead support pad is disclosed in U.S. Pat. No. 7,069,932 ("the '932 patent") the contents of which are incorporated herein by reference.

The present invention also contemplates that the forehead pad support be separable from the forehead arm and/or that the forehead pad support can be attached to the forehead arm such that the forehead pad support is moveable relative to the forehead arm. These techniques for attaching forehead pad support to the forehead arm are also taught in the '932 patent.

Forehead pad 62 is made from any material, such as gel, foam, silicone, or any combination thereof, suitable for contacting the surface of the user. In addition, the forehead pad is attached to the forehead pad support in any conventional manner, and may be permanently attached to or separable from the forehead pad support. While a single forehead pad is shown in the figures, the present invention contemplates that multiple pads may be provided. Moreover, each for forehead pad can have any desired configuration. As example of a configuration that allows the forehead pad to "self-align" on the user and that is suitable for use in the present invention is disclosed in U.S. patent application Ser. No. 10/884,060 (publication no. US-2005-0011522-A1) the contents of which are incorporated herein by reference.

Because the patient interface of the present invention is intended for use in a non-invasive ventilation-type of ventilation/pressure support system, an exhaust assembly 66 is provided along the gas flow path to allow the patient's exhaled gasses to vent to atmosphere. In the present embodiment, exhaust assembly 66 is provided in a coupling member 46. The present invention also contemplates proving the exhaust assembly in the patient interface, such as in the seal member of the patient interface, the faceplate, or at a plurality of such locations. Placing the exhaust assembly close the patient interface minimizes the deadspace in the breathing circuit.

The present invention contemplates that exhaust assembly 66 can have any configuration, so long as the function of exhausting a sufficient amount of gas to atmosphere is achieved. For example, the exhaust assembly can be configured to provide a continuous flow rate for the venting of exhaust gas to atmosphere, or can be configured to provide a variable flow rate; dependent, for example, on the pressure of the gas in the closed system. In the illustrated embodiment, exhaust assembly 66 is defined by a plurality of vent holes 68 provided in the wall of coupling member 46. The number, size, hole pattern, and shape of the holes can have any configuration. One example of a multiple-hole type of exhaust assembly suitable for use in the present invention is disclosed in U.S. Pat. No. 6,851,425, the contents of which are incorporated herein by reference. It should again be emphasized that any suitable exhaust configuration, located at any suitable position, on or near the patient interface can be used with the patient interface of the present invention.

Patient interface 30 includes an adjustment mechanism 70 that allows the position of seal member 38 relative to faceplate 36 to be adjusted from a first position to a second position. Adjustment mechanism 70 also maintains the seal member in the second position during use of the patient interface. In the illustrated exemplary embodiment, the user actuates the adjustment mechanism by rotating a knob portion 72, as indicated by arrow C in FIG. 3. As discussed in detail below, this causes an upper portion of seal member 38 to be pushed away from or pulled toward faceplate 36, as indicated by arrow D. Because the seal member is relatively flexible, this pushing or pulling changes the contact of the seal member of the surface of the user, thereby allowing the user to adjust the seal member to fit their particular facial structure or comfort needs. This can be done while the patient interface is donned on the user.

Figure 3:
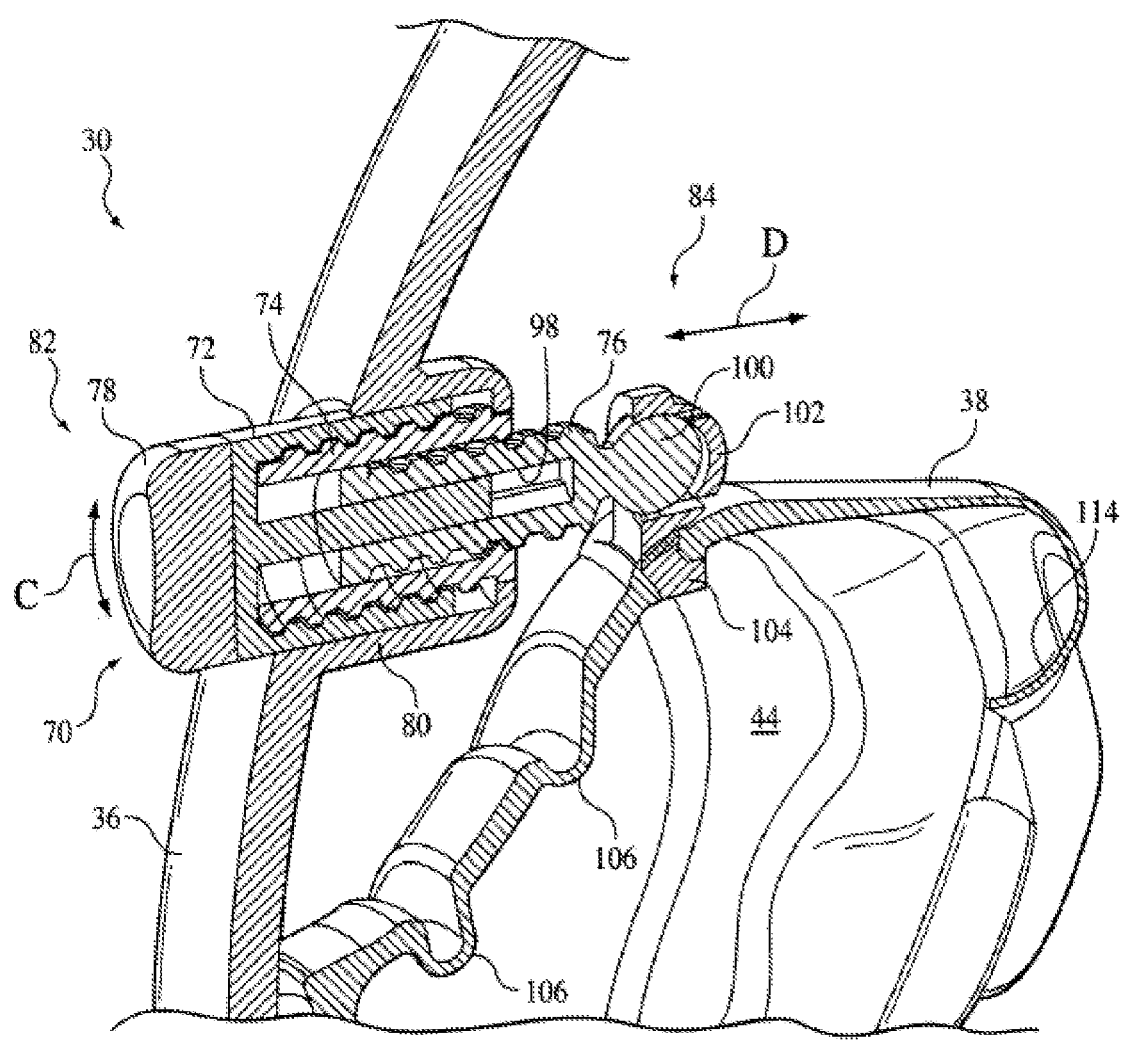
FIG. 3 is a sectional view of the adjustment mechanism in the patient interface of FIG. 1.
Figure 4:
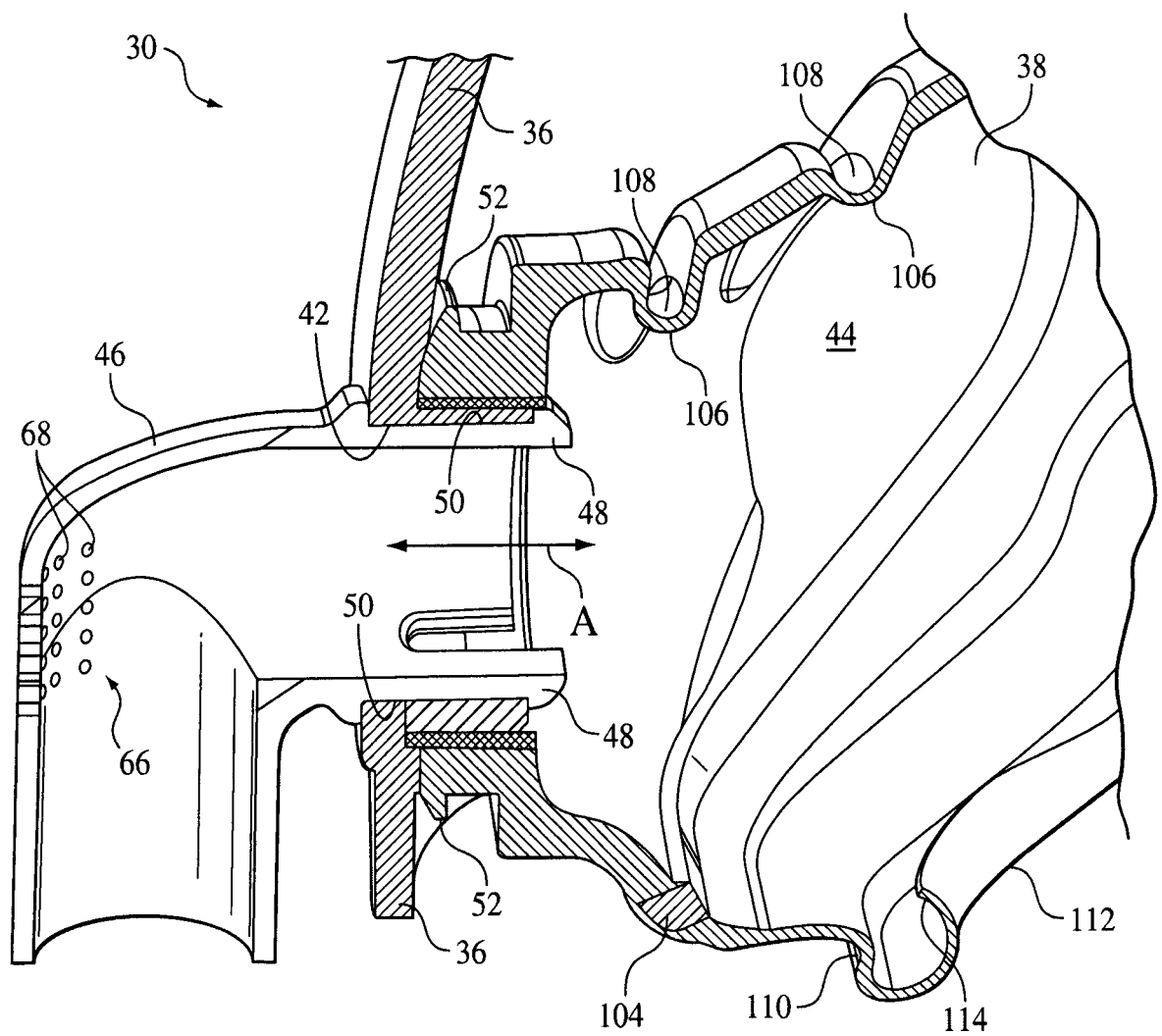
FIG. 4 is a sectional view of the seal member and faceplate coupling configuration in the patient interface of FIG. 1.
Figure 5:
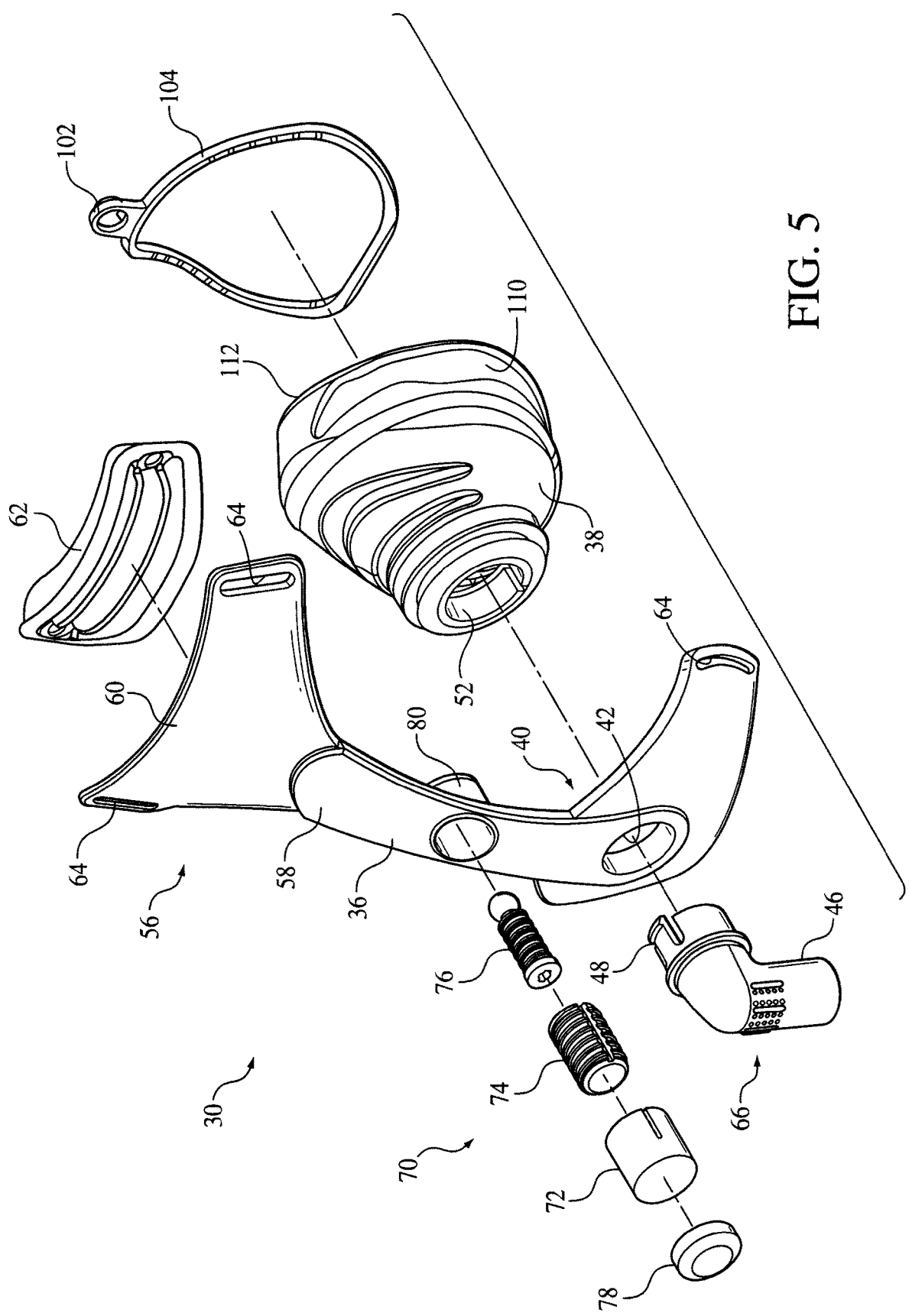
FIG. 5 is an exploded view of the patient interface of FIG. 1.
Figure 6:
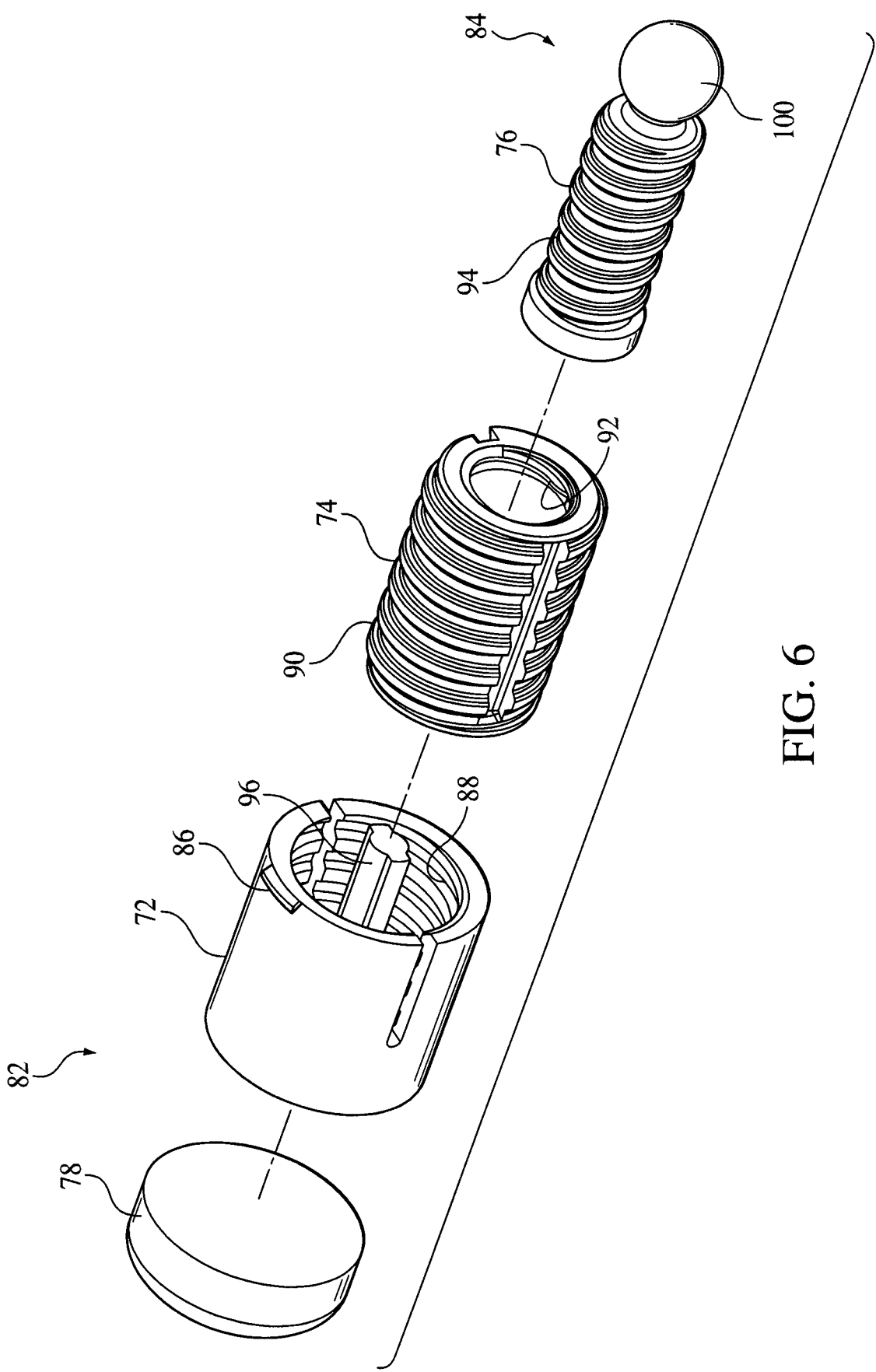
FIG. 6 is an exploded view of the adjustment mechanism in the patient interface of FIG. 1.
Figure 7:
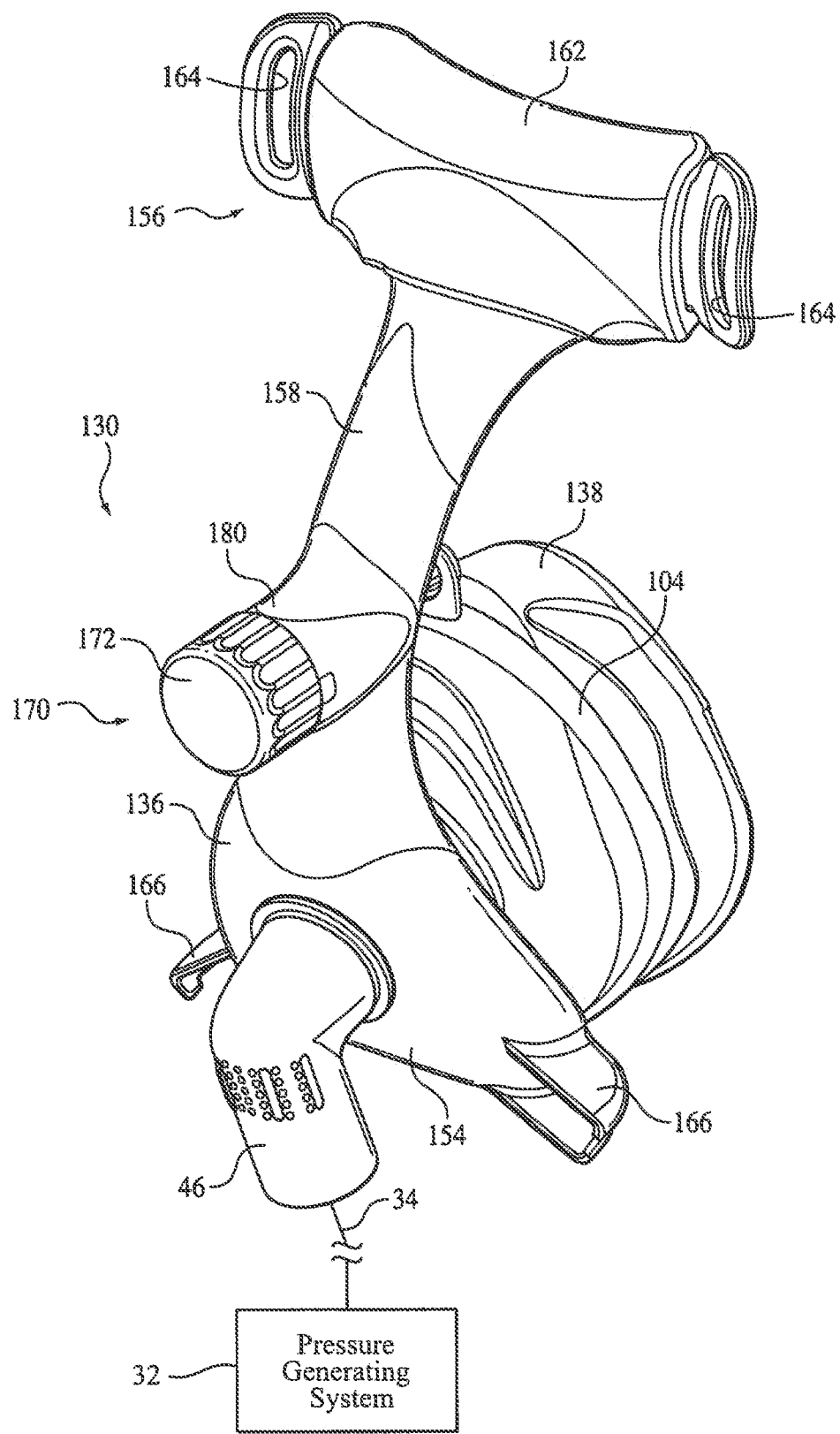
FIG. 7 is a front perspective view of a second embodiment of a patient interface according to the principles of the present invention shown schematically connected to a pressure support system.
Figure 8:
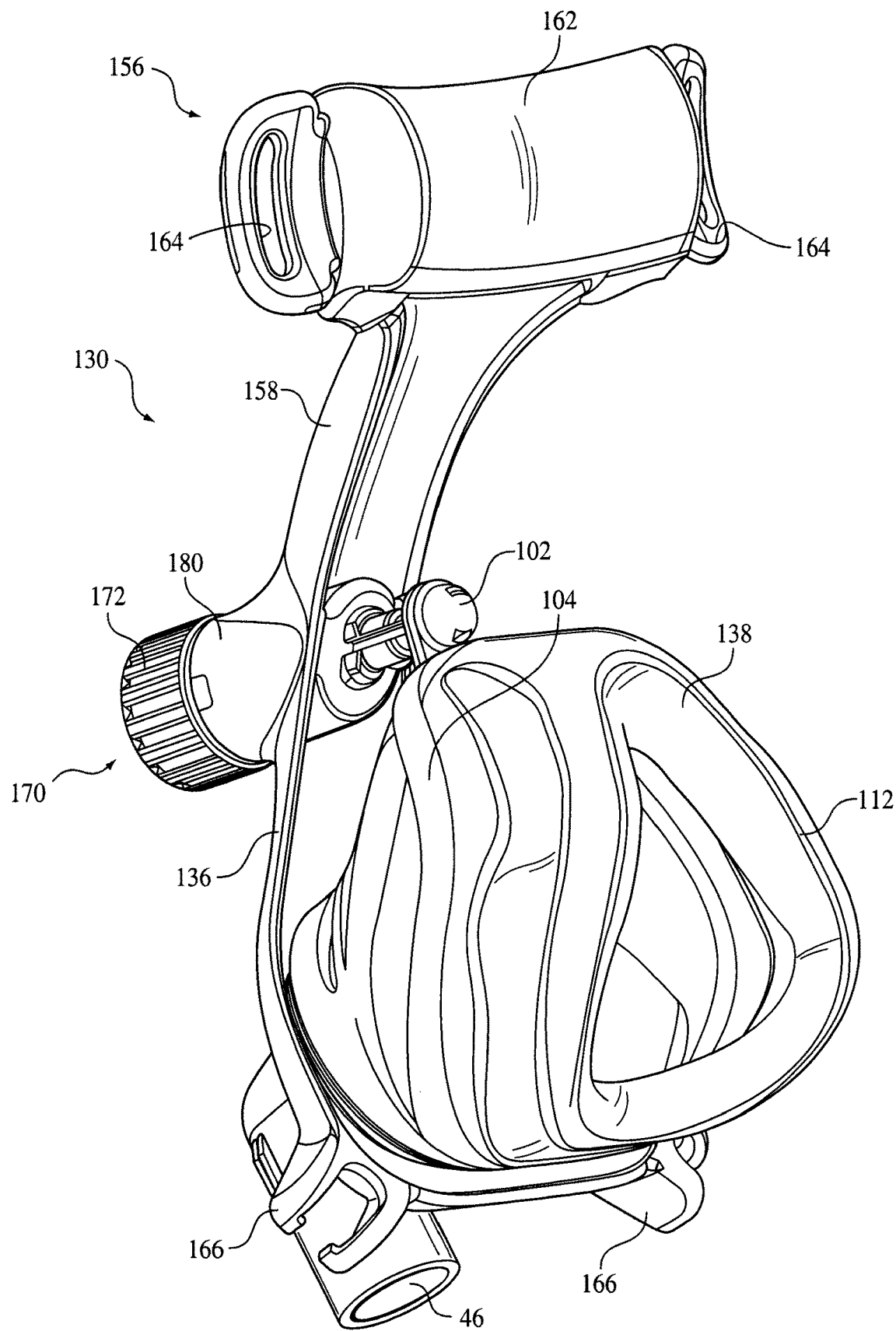
FIG. 8 is a rear perspective view of the patient interface of FIG. 7.
Figure 9:
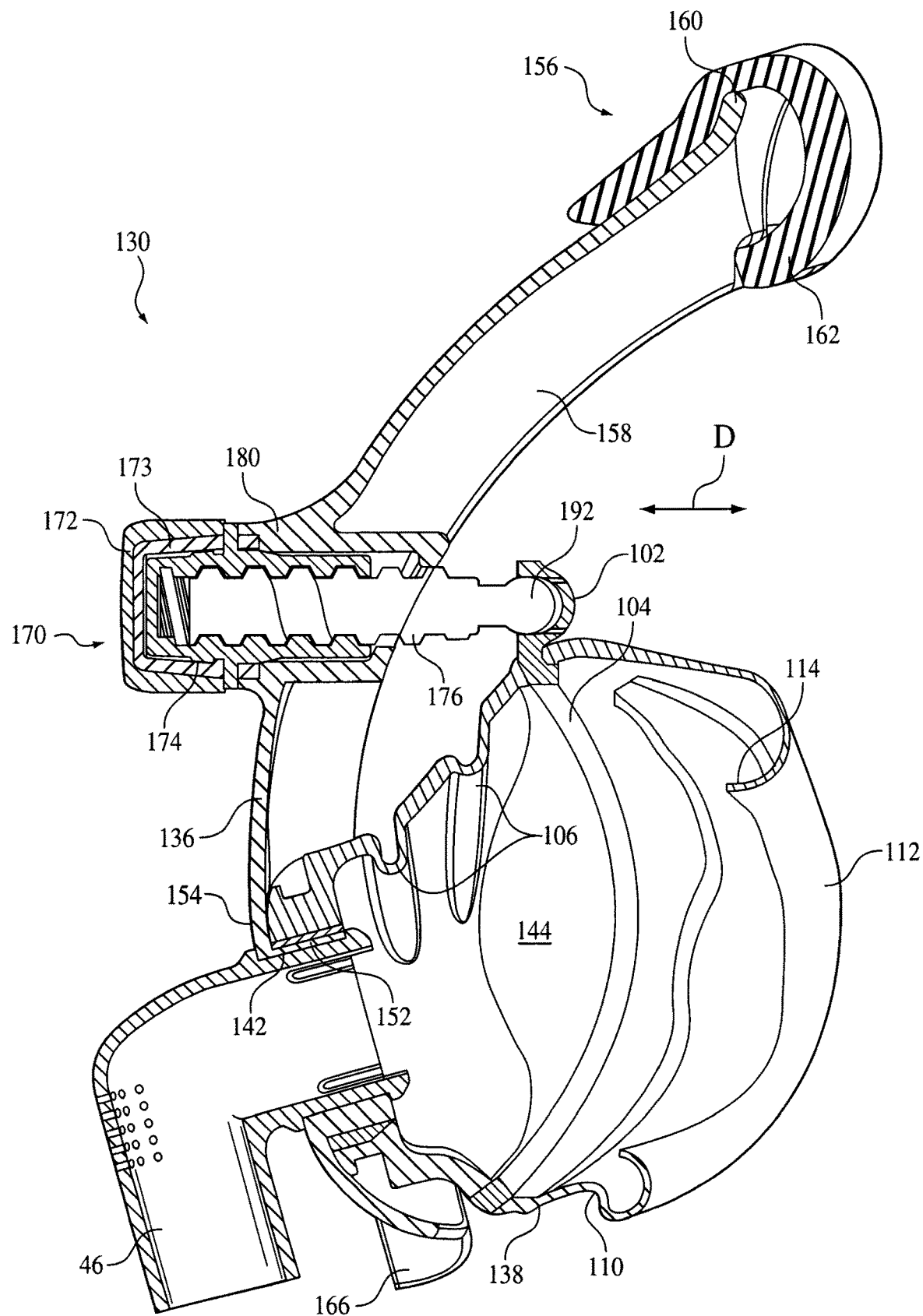
FIG. 9 is a side sectional view of the patient interface of FIG. 7.
Figure 10:
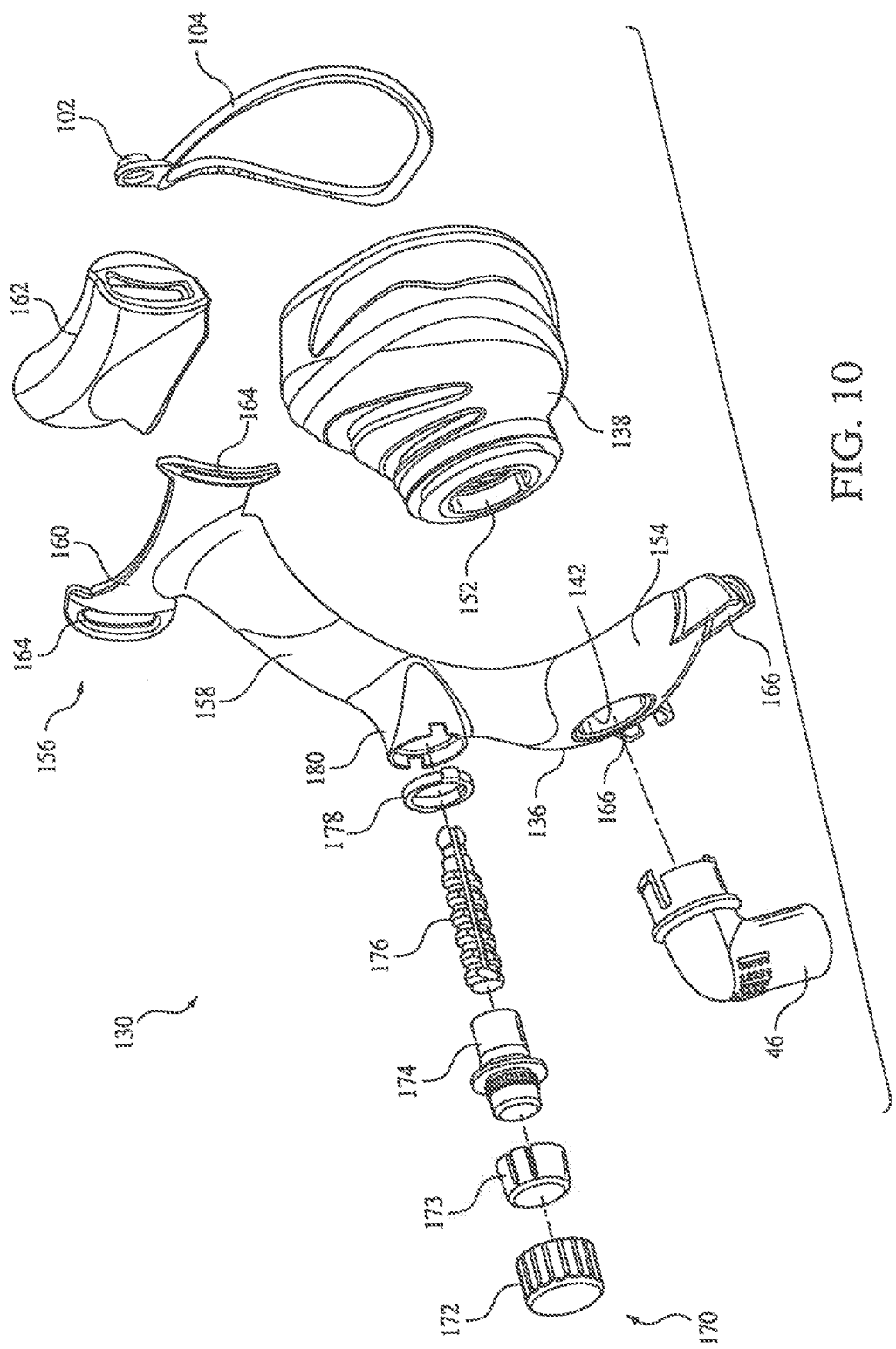
FIG. 10 is an exploded view of the patient interface of FIG. 7.
Figure 11:
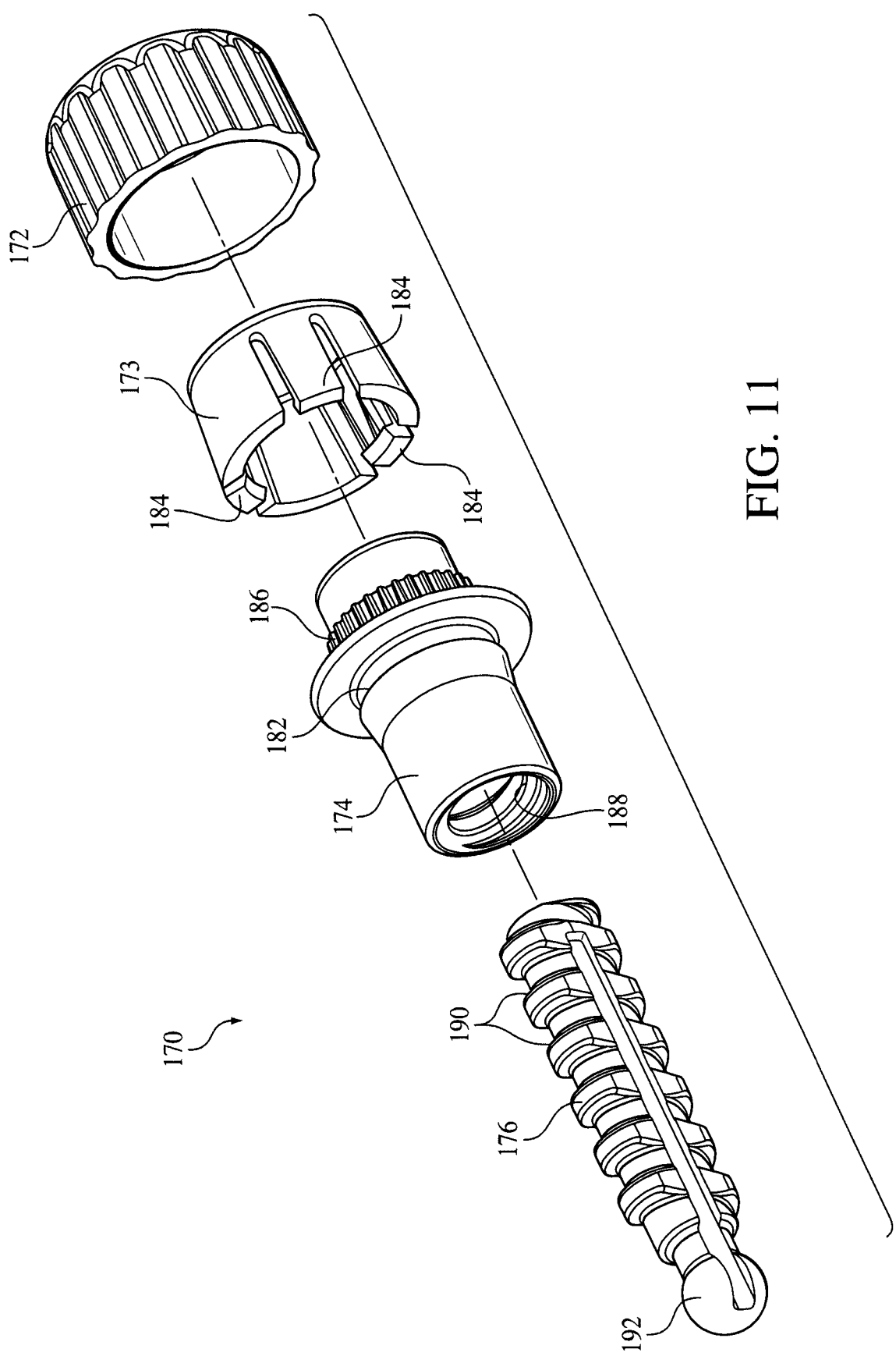
FIG. 11 is an exploded view of the adjustment mechanism in the patient interface of FIG. 7.

An exemplary embodiment of adjustment mechanism 70 according to one embodiment of the present invention is shown, in detail, in FIGS. 3 and 6. Adjustment mechanism 70 is coupled to faceplate 36 and seal member 38 and includes knob portion 72, barrel member 74, and stem 76. In the illustrated embodiment, a cap 78 is attached to knob portion 72. Of course, the cap and knob portion can be formed from a single piece. Many of the components of the adjustment mechanism are disposed in a recess 80 provided in faceplate 36 so a manually actuatable portion 82 is exposed at the front of the mask and a seal member contacting portion 84 is disposed on the opposite side of the faceplate and engages the seal member.

Knob portion 72 is secured within recess 80 so that it is free to rotate within the recess but does not pull out from the recess. In an exemplary embodiment, a pair of tabs 86 are provided in an outer surface of the knob portion. These tabs insert into a channel defined on an inner wall of the recess so that once the tabs are engaged in the channel, the knob portion is rotatably secured to the faceplate. Rotating knob portion 72 causes barrel member 74 to also rotate due to threads 88 provided on an interior surface of the knob portion engaging a corresponding threads 90 provided on an exterior surface of the barrel member. Barrel member 74 does not move relative to the faceplate when it is rotated. A tab or lip 92 is provided on the end of the barrel member that engages threads 94 provided on stem 76. Thus, as the barrel member rotates in a fixed position, the lip engaging the threads of the stem cause the stem to move, as indicated by arrow D. An optional alignment member 96 provided on knob portion 72 inserts into a channel 98 defined in stem 76 to keep the stem properly aligned as it moves inward and outward relative to the faceplate.

Adjustment mechanism 70 is coupled to seal member 38 such that the adjustment mechanism moves at least an upper portion of the seal member relative to the faceplate—the upper portion of the seal member being the portion that is disposed over the bridge of the user's nose when the patient interface is worn by the user. In the illustrated exemplary embodiment, a ball-and-socket connection is used to couple the adjustment mechanism to the seal member. More specifically, a ball 100 is provided on the end of stem 76 and a socket 102 is provided on seal member 38. Of course, the present invention contemplates that the location of the ball-and-socket can be reversed.

The use of this type of connection provides a high degree of freedom of movement for the seal member so that the whole seal member does not simply mover linearly with respect to the faceplate when the adjustment mechanism is actuated. Instead, this configuration allows the upper is allowed to move on one direction, e.g., to be pushed away from the faceplate, while the lower portion at the opposite end of the seal member is moves in an opposite direction, e.g., is pushed toward the faceplate. In essence, the seal member is capable of being pivoted, articulated, or otherwise moved relative to the faceplate by this type of connection between the adjustment mechanism and the seal member. This connection also allows the seal member to move side-to-side so that the seal member is properly seated on the user. It is to be understood that the present invention contemplates using other connecting techniques to join the attachment mechanism with the seal member, including providing a rigid connection of the adjustment mechanism to the seal member so that the seal member does more linearly with respect to the faceplate.

A generally rigid annular ring 104 is disposed around the perimeter of seal member 38 to provide a secure attachment point for the adjustment mechanism to the seal member. The present invention contemplates attaching ring 104 to the seal member using any conventional technique, such as adhering, mechanically coupling, or two-shot molding the ring to the seal member. Grooves may be provided in the seal member in which the ring is seated. In addition, the ring need not extend around the entire perimeter of the seal member. The present invention also contemplates that the annular ring can make out of the same material of the sealing member, but with thicker section.

In the illustrated exemplary embodiment, seal member 38 includes at least one pleat 106 (which can also be referred to as a fold or gusset) provided at a portion of the seal member so that the seal member has the desired degree of flexibility. In this case, pleats 106 are provided at and upper portion of the seal member so that this portion of the seal member can expand and contract with adjustment of the adjustment mechanism. Pleats 106 are oriented such that the pleat protrudes into chamber 44 with a channel 108 defined on the exterior surface of the seal member. Of course, the present invention contemplates orienting the pleats in the opposite direction or eliminating them entirely. In addition, the number, size, configuration, and location of the pleats on the seal member can also be varied so that the seal member flexes where desired.

A pleat 110 is also provided at or near a patient contacting portion 112 of the seal member to control the collapsibility of the patient contacting portion of the seal. An example of such a pleat is disclosed in U.S. patent application Ser. No. 11/312,026 (publication no. US-2006-0130844-A1), the contents of which are incorporated herein by reference.

A flap 114 is provided at patient contacting portion 112 of the seal member to provide a good seal between the seal member and the surface of the user. Flap 114 extends around a perimeter of the seal member. Of course, the present invention also contemplates providing flap 114 only at selected locations along the perimeter of the seal. In addition, the present invention contemplates providing multiple flaps at the patient contacting portion.

Seal member 38 can be made from any suitable material, such as gel, an air filled bladder, silicone, foam, rubber, or combination of materials, as is known to those skilled in the art. Thus, a complete listing of all possible materials or combinations of materials suitable for use in the seal member is omitted from the present application for purposes of brevity. Seal member 38 can also have any one of a variety of configurations. For example, the seal member can be a nasal seal that seals only over the user's nose or a nasal/oral seal that seals over the nose and mouth. Again, the art is replete with different seal configurations. To the extent that any of these different configurations can be used in the patient interface of the present invention, the present invention contemplates doing so.

FIGS. 7-11 illustrate a second, albeit similar, embodiment of a patient interface 130 according to the principles of the present invention. Patient interface 130 includes a faceplate 136 and a seal member or cushion 138, which is coupled to the faceplate such that a chamber 144 define by the seal member communicates with patient circuit 34 via an orifice 142 defined in the faceplate. As in the previous embodiment, coupling member 46 is rotatably coupled to the faceplate so that gas can flow to and from the airway of the user through the patient interface. Seal member 138 is coupled to the faceplate by means of a ring 152 to which the seal member is secured. The seal member is either fixed to the faceplate or is rotatable relative thereto. The present invention also contemplated that ring 152 can be eliminated and the seal member can be attached to the faceplate (rotatable or fixed) using any conventional technique.

Faceplate 136 includes a body portion 154 to which is coupled the seal member, and a forehead arm 158 that supports a forehead support 156. Forehead support includes a forehead pad support 160 and a forehead pad 162 coupled thereto. In this embodiment, the forehead pad is a flexible cushion that slips over the forehead pad support. A pair of slots 164 are provided on the forehead pad support to function as the headgear attachment members. It should be expressly understood that the alternative embodiments for the various features of the patient interface, including the faceplate, seal member, forehead arm, forehead support, forehead pad support, forehead pad, and headgear attachment members discussed above are equally applicable to this embodiment, as well as the other embodiments discussed herein.

One difference between patient interface 130 and patient interface 30 on the previous embodiment, is the configuration for headgear attachment members 166 provided on body portion 154 of faceplate 136. In this embodiment, headgear attachment members 166 are sockets for receiving ball clips (see headgear clips 265 in FIGS. 12-14) that are attached to the headgear straps. Examples of various configurations for a ball-and-socket type of headgear attachment is disclosed in U.S. patent application Ser. No. 10/629,366 (publication no. US-2004-0025883-A1) the contents of which are incorporated herein by reference.

Another difference between patient interface 130 and patient interface 30 on the previous embodiment resides in the configuration for an adjustment mechanism 170 that controls the position of seal member 138 relative to faceplate 136. Adjustment mechanism 170 provides the same function, i.e., moves the upper portion of the seal member relative to the faceplate, as that of the previous embodiment, but has a different configuration for doing so. Adjustment mechanism 170, which is perhaps best shown in FIGS. 9-11, includes a knob portion 172, a ratchet member 173, a barrel member 174, and a stem 176 and is coupled to faceplate 136 via a protrusion 180, where a channel is defined in the faceplate to house the components of the adjustment mechanism. A lock ring 178 secures barrel member 174 to the faceplate by engaging both the faceplate and a channel 182 defined in the barrel member.

Knob portion 172 is attached to ratchet member 173 using any conventional technique, such as by a friction engagement. Ratchet mechanism 173 include prongs 184 that engage teeth 186 provided on barrel member 174 so that rotating the knob portion and the ratchet member also rotates the barrel member. The barrel member includes threads 188 on an interior surface that engage threads 190 provided on an exterior surface of stem 176. As a result, rotating barrel member 174 causes stem 176 to move relative to the faceplate, as indicated by arrow D in FIG. 9, within the interior of the barrel member, which does not move. As in the embodiment of FIGS. 1-6, the end of the stem is coupled to seal member 138 via a ball 192 provided at the end of the stem and a socket 102 provided on a ring 104 that is coupled to the seal member using any conventional technique. The ratchet mechanism of this embodiments prevent over-tightening of the adjustment mechanism in either direction (inward or outward) because on the end of travel is reached, prongs 184 begin to flex away from teeth 186 so that they slip over teeth and prevent the ratchet member from rotating the barrel member.

In the embodiments for the patient interface discussed above with respect to FIGS. 1-11, the seal member is relatively free-floating with respect to the faceplate. In other words, control of the position of the patient contacting portion seal member relative to the faceplate is provided by the attachment mechanism. The seal member is relatively free to move side-to-side, i.e., along a horizontal axis, but movement along a vertical axis is controlled by the attachment mechanism. Of course, the seal member is also connected to the faceplate at orifice 42 or 142, but this connection does not control the position of the patient contacting portion of the seal member. It merely serves to couple the seal member to the faceplate. The present invention, however, contemplates providing other attachment points between the seal member and the faceplate to control the position of the patient contacting portion of the seal member so that the user can adjust or control the contact of the seal on his or her face to optimize comfort and sealing ability.

Figure 12:
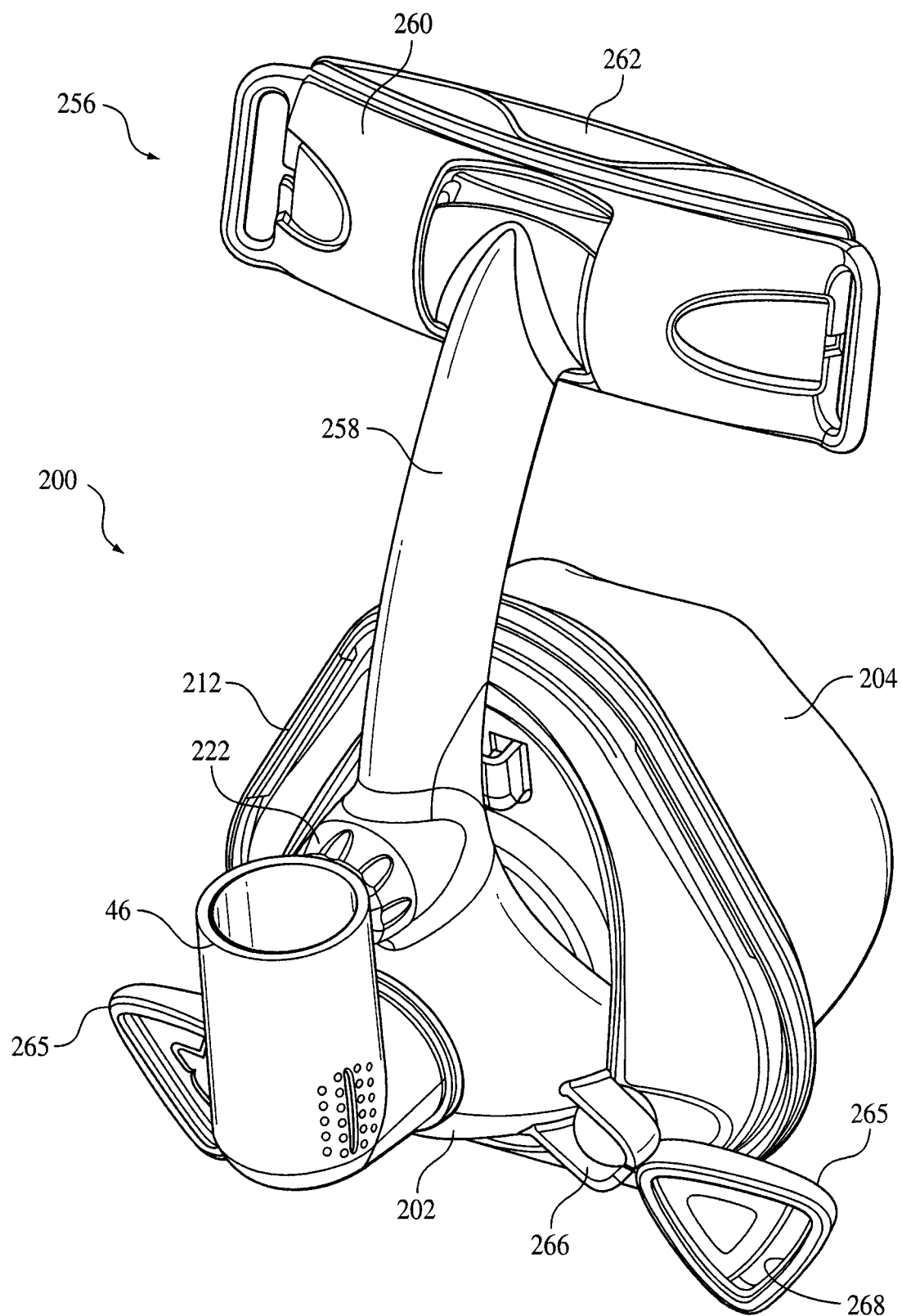
FIG. 12 is a front perspective view of a third embodiment of a patient interface according to the principles of the present invention.
Figure 13:
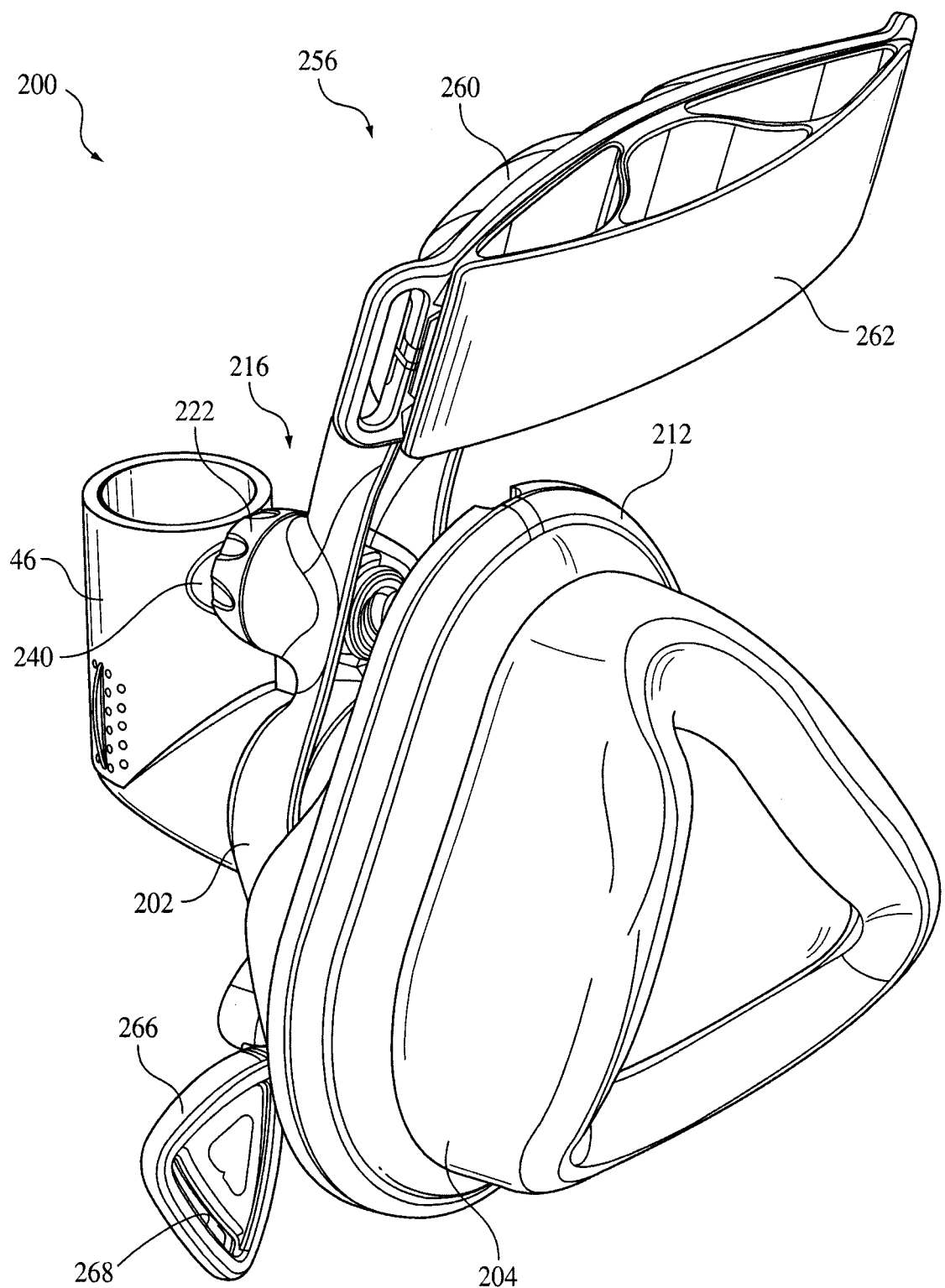
FIG. 13 is a rear perspective view of the patient interface of FIG. 12.
Figure 14:
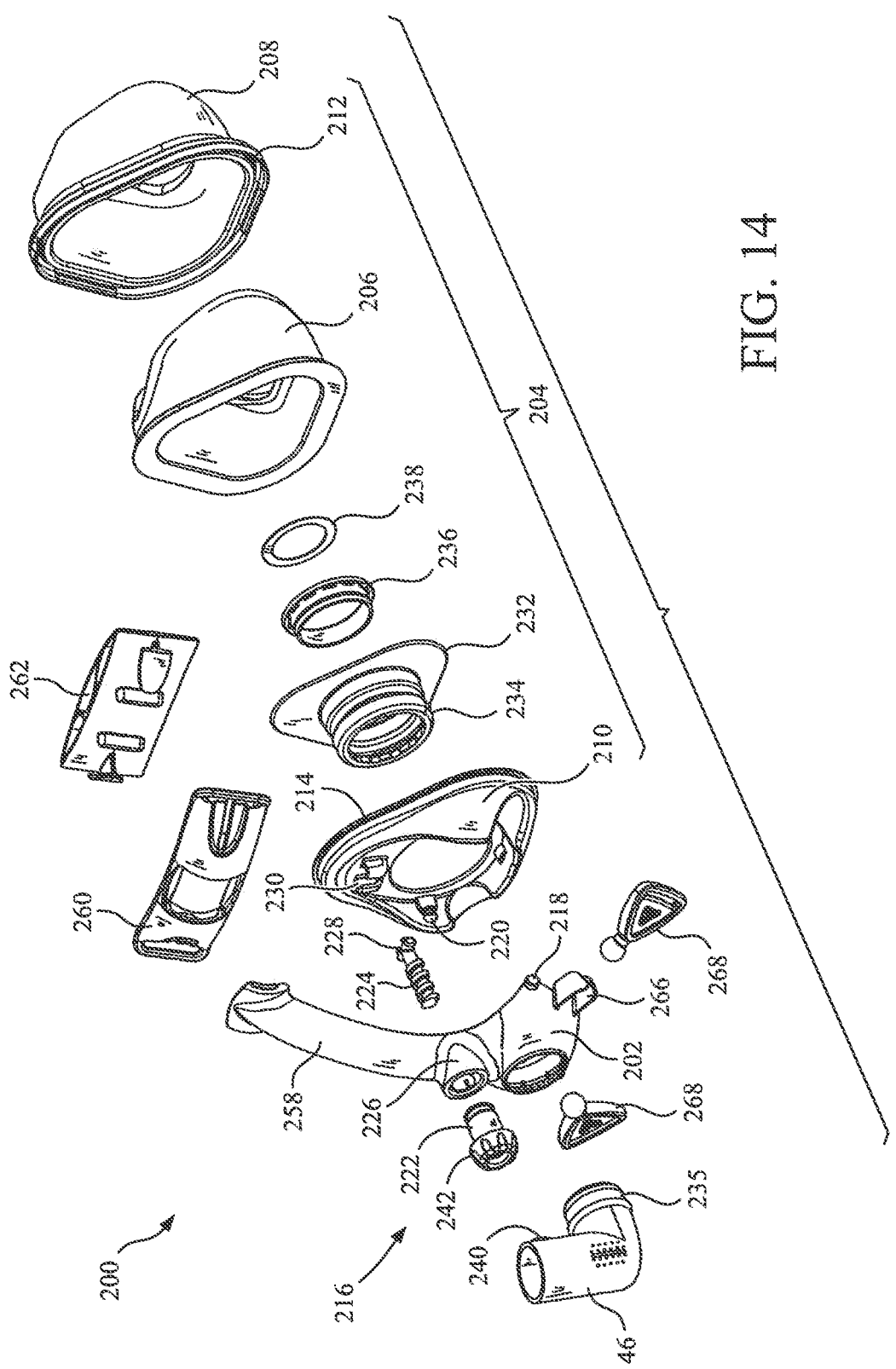
FIG. 14 is an exploded view of the patient interface of FIG. 12.

FIGS. 12-14 illustrate an example of a third embodiment for a patient interface 200 that includes multiple contact points between faceplate 202 and a seal member 204 to provide greater control over the position of the patient contacting portion of the seal member relative to the faceplate than in the previous embodiments. In this embodiment, seal member 204 comprises a cushion 206, a flap 208, and a seal mount member 210. In this particular embodiment, flap 208 includes an attachment ring 212 that snaps onto an outer edge portion 214 of the seal mount member capturing the cushion between the seal mount member and the flap. In the assembled configuration, the seal member.

The seal member is coupled to the faceplate by engaging the seal mount member with the faceplate at three attachment points. Two of the attachment points are at the lower left and right sides of the seal mount member, and the third is the attachment between the seal mount member and the faceplate provided by adjustment mechanism 216. More specifically, a pair of pivot members 218 (only one of which is illustrated) are provided on each side of faceplate 202, and a corresponding pair of pivot member couplings 220 are provided on seal mount member 210 (only one of which is illustrated). When assembled, the pivot members rotate within the pivot member couplings to allow two-dimensional movement, i.e., rotation about an axis defined between the pivot members, of the seal member relative to the faceplate under the control of the adjustment mechanism. There is little or no side-to-side movement of the seal member relative to the faceplate.

In this embodiment, adjustment mechanism 216 includes a knob portion 222 and a stem 224. The knob portion and a protruding portion 226 of faceplate 202 are coupled such that the knob portion rotates within relative to the faceplate but remains coupled thereto. The knob portion includes internal threads that engage the external threads on the stem so that rotating the knob portion causes the stem to move axially within the knob portion. An end portion 228 of the step is rotatably coupled to a mounting member 230 provided on seal mount member 210. Of course, a ball-and-socket coupling between the step and the seal mount member is also contemplated by the present invention, as are other coupling techniques, including fixed couplings.

Seal member 204 also includes a sealing gasket 232 that couples the seal member to coupling member 46. Sealing gasket 232 includes a flexible neck portion 234 that couples to a coupling portion 235 of the coupling member. The neck portion is flexible to allow the seal member to move relative to the faceplate. A lock ring 236 and a washer 238 are provided to couple the sealing gasket to the coupling member. It is to be understood that the present invention contemplates using any conventional technique to couple the seal member to the patient circuit and/or coupling member 46. In an exemplary embodiment, the coupling between the seal member to the patient circuit and/or coupling member is a rotatable coupling so that the position of the patient circuit relative to the patient interface can be changed.

Another feature of patient interface 200 is that knob portion 222 and coupling member 46 are configured such that the coupling member can be selectively secured to the knob portion. The allows the patient circuit to be maintained in an over-the-head relationship on the user, which is desirable to some. When not attached to knob portion 222, the coupling member and patient circuit can move freely, e.g., rotate relative to the faceplate, which is also desirable to some patients so that they can position the breathing circuit at a location that best suits them. In an exemplary embodiment, coupling member 46 includes a protrusion 240 and knob portion 222 includes a recess 242 adapted to receive the protrusion when the coupling member is dispose over the knob portion. Thus, the engagement of the protrusion in the recess secures the coupling member to the faceplate. Of course, the location of the protrusion and recess can be reversed. In addition, other techniques for coupling (permanently or selectively) the coupling member and/or patient circuit to the faceplate are contemplated by the present invention.

As in the previous embodiments, patient interface 200 includes a forehead support 256 that is supported by a forehead arm 258. In the illustrated exemplary embodiment, forehead support 256 includes a forehead pad support 260 that is rotatably connected to the forehead arm. A forehead pad 262 is coupled to the forehead pad support. In this embodiment, the forehead pad is a silicone pad that is selectively attached to the forehead pad support. Of course, other configurations, materials, sizes, etc. for the forehead pad are contemplated by the present invention, as are other configurations, materials, sizes, etc. for the forehead pad support and forehead arm.

A headgear assembly (not shown) attaches the patient interface on the head of the user. The headgear assembly includes straps that attach to the patient interface via headgear slots 264 provided in forehead pad support and via headgear clips 265. Headgear clips 265 attach to headgear attachment members 266 provided on faceplate 202 via a ball-and-socket configuration and include slots 268 into which the headgear straps are inserted.

Figure 15:
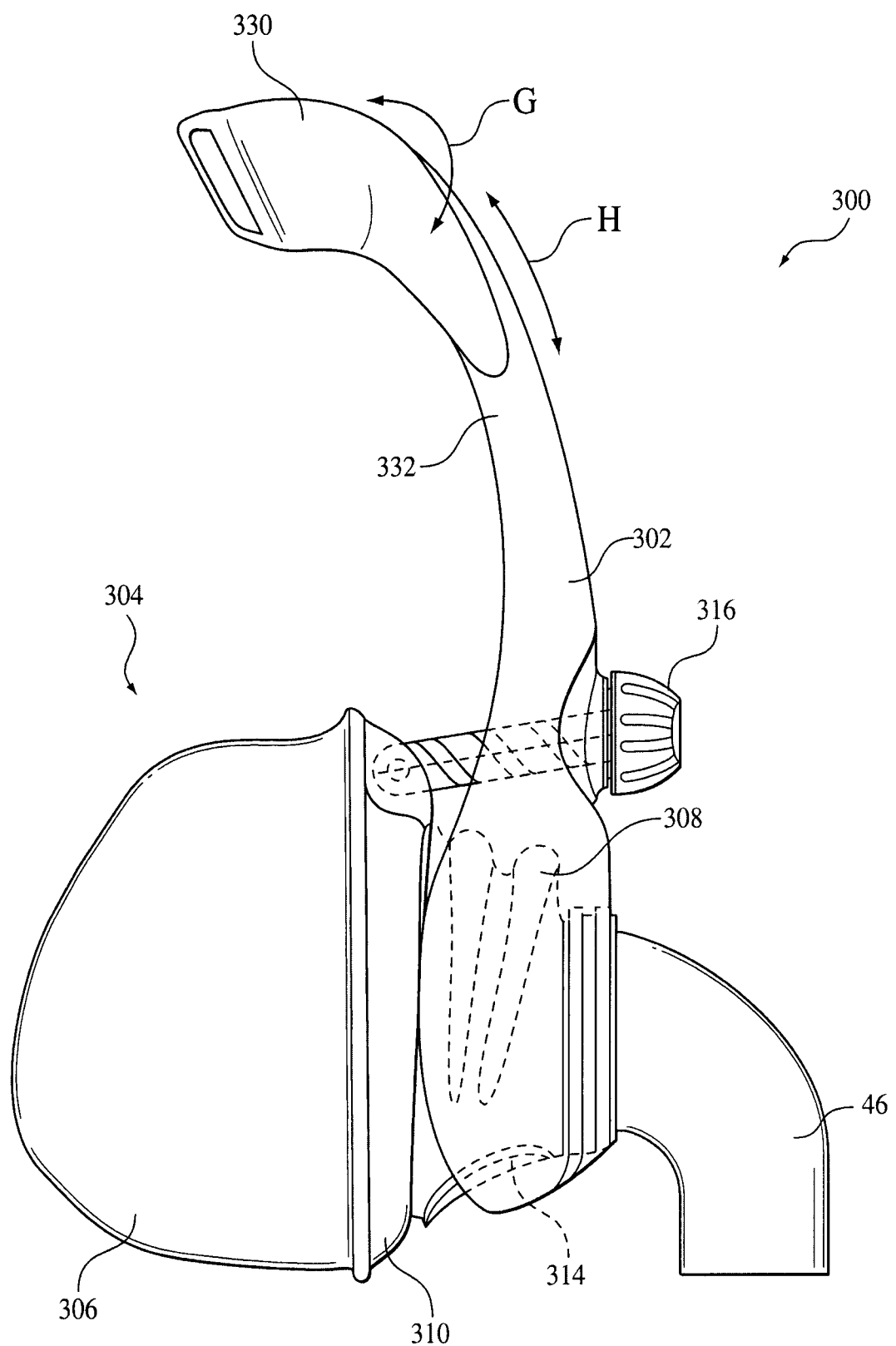
FIG. 15 is a side view of a fourth embodiment of a patient interface according to the principles of the present invention.
Figure 16A:
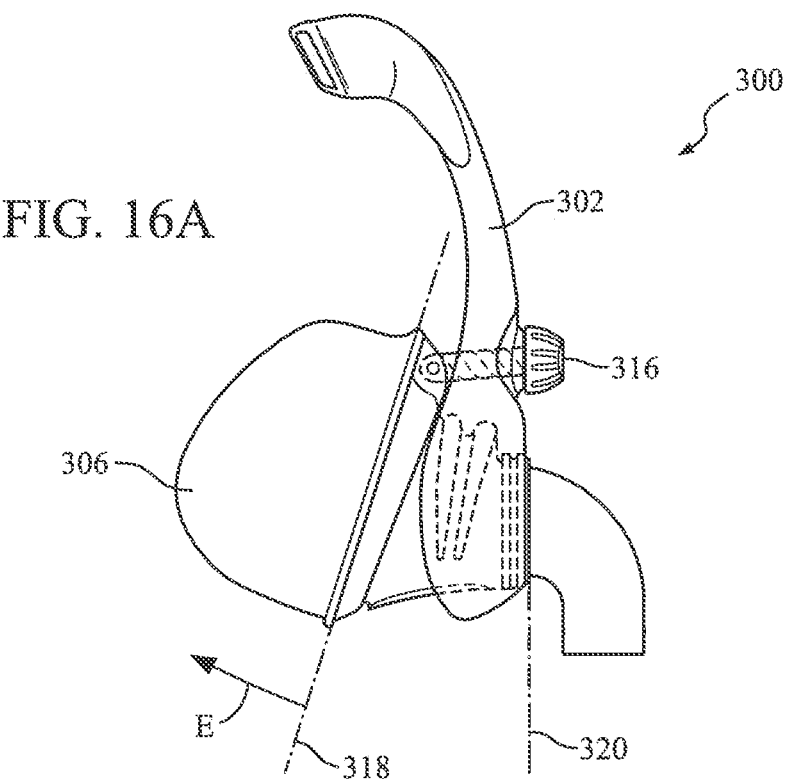
FIGS. 16A and 16B are side views showing the adjustment of the seal member relative to the faceplate in the patient interface of FIG. 15.
Figure 16B:
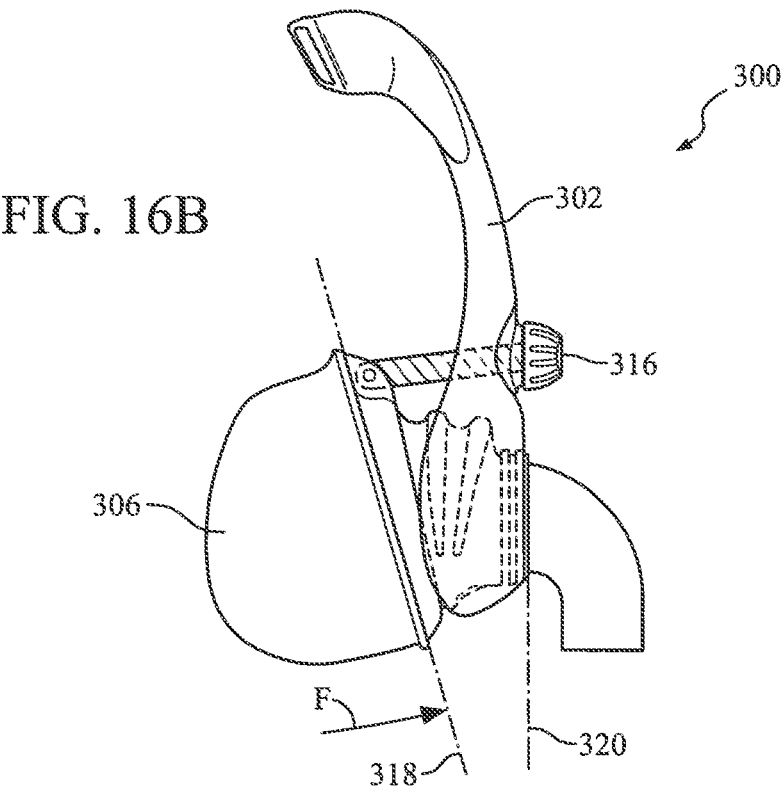
Figure 17:
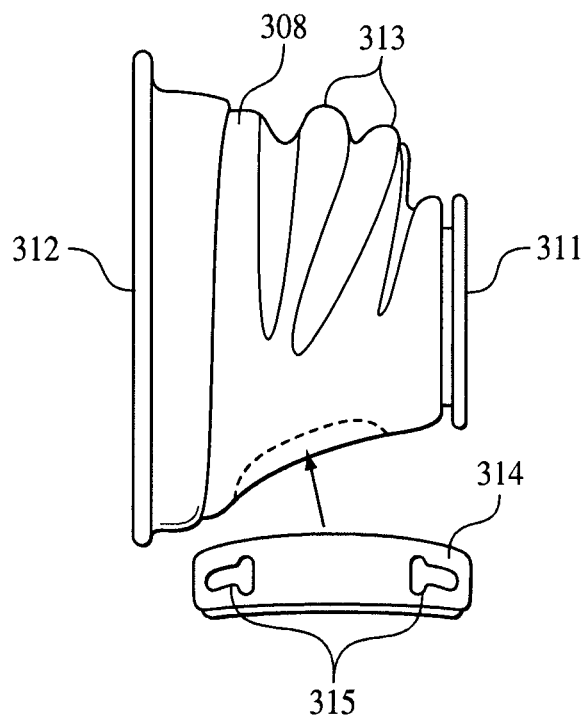
FIG. 17 is a side view of the seal member in the patient interface of FIG. 15.

FIGS. 15-17 illustrate a fourth embodiment of a patient interface 300 according to the principles of the present invention. Patient interface 300 includes a faceplate 302 and a seal member 304 coupled to the faceplate. The seal member includes a cushion 306, a collar 308, and a seal mount member 310 to which the cushion and collar are mounted or otherwise attached. The seal mount member is coupled to the faceplate via and adjustment mechanism 316. The seal member is also coupled to the faceplate via collar 308, which communicates the interior of the seal member with coupling member 46.

As best illustrated in FIG. 17, collar 308 includes a first end portion 311 that attaches to faceplate 302, coupling member 46, the patient circuit, or any combination thereof. A second end portion 312 attaches to seal mount member 310. Collar 308 is formed from a flexible or material or is structured so as to be flexible so that the position of the seal member can be adjusted relative to the faceplate while allowing gas to communicate between the patient circuit and the interior of the seal member. In the illustrated embodiment, the flexibility of the seal is enhanced by a plurality of pleats 313 defined in the wall of the collar between the first and second end portions. Of course, other sizes, configurations, and locations for the pleats are contemplated by the present invention.

Seal member 304 also includes a retaining member 314 coupled to the wall of collar 308. Retaining member 314 provides structural support for the collar to help keep the seal member properly positioned in the user. In an exemplary embodiment of the present invention, retaining member 314 is a flexible metallic band that is attached to the lower portion of the collar. A pair of attachment members 315 are provided for attaching the band on the collar. It is to be understood that the present invention contemplates that the size, shape, degree of flexibility, location, number, and material of the retaining member can be varied depending the support needs for the collar.

As noted above, in this embodiment and in the previous embodiments, adjustment mechanism 316 control the position of the seal member relative to the faceplate. This is demonstrated in FIGS. 16A and 16B, where FIG. 16A shows the upper portion of the seal member moved close to the faceplate (the full inward position) and FIG. 16B shows the upper portion of the seal member moved away from the faceplate (the fill outward position). It should be noted that when the adjustment mechanism is in the inward position, a first plane 318 generally defined by the seal member, intersects a second plane 320 generally defined by the faceplate, at a location somewhere above the adjustment mechanism. In addition, the bottom portion of the seal member moves away from the frame, as indicated by arrow E. On the other hand, when the adjustment mechanism is in the outward position, first plane 318 intersects a second plane 320 at a location somewhere below the adjustment mechanism, and the bottom portion of the seal member moves toward the frame, as indicated by arrow F.

While FIGS. 16A and 16B show the bottom of the seal member as moving, the present invention also contemplates that the seal member can be configured and arranged such that a portion of the seal member, such as the lower portion, does not move. Instead, it can act as a pivot point for the rest of the seal. For example, the bottom portion of the can be made thick, made from a less flexible material, includes support structures, or any combination thereof so that it is relatively non-flexible. In which case, the rest of the seal would move about this pivot point. Of course, this type of pivot point can be provided at other locations of the seal member.

Seal member 300 includes a forehead support 330 provided on a forehead arm 332. Forehead support supports a forehead pad (not shown) and can be fixed to the support arm. However, the present invention also contemplates that forehead support 330 rotate relative to the forehead arm, as indicated by arrow G, so that the forehead pad is properly seated or aligned on the surface of the user. The present invention further contemplates that the forehead support is moveable along the forehead arm, as indicated by arrow H, so that the position of the forehead pad can be adjusted to suit the needs of the user.

Figure 20:
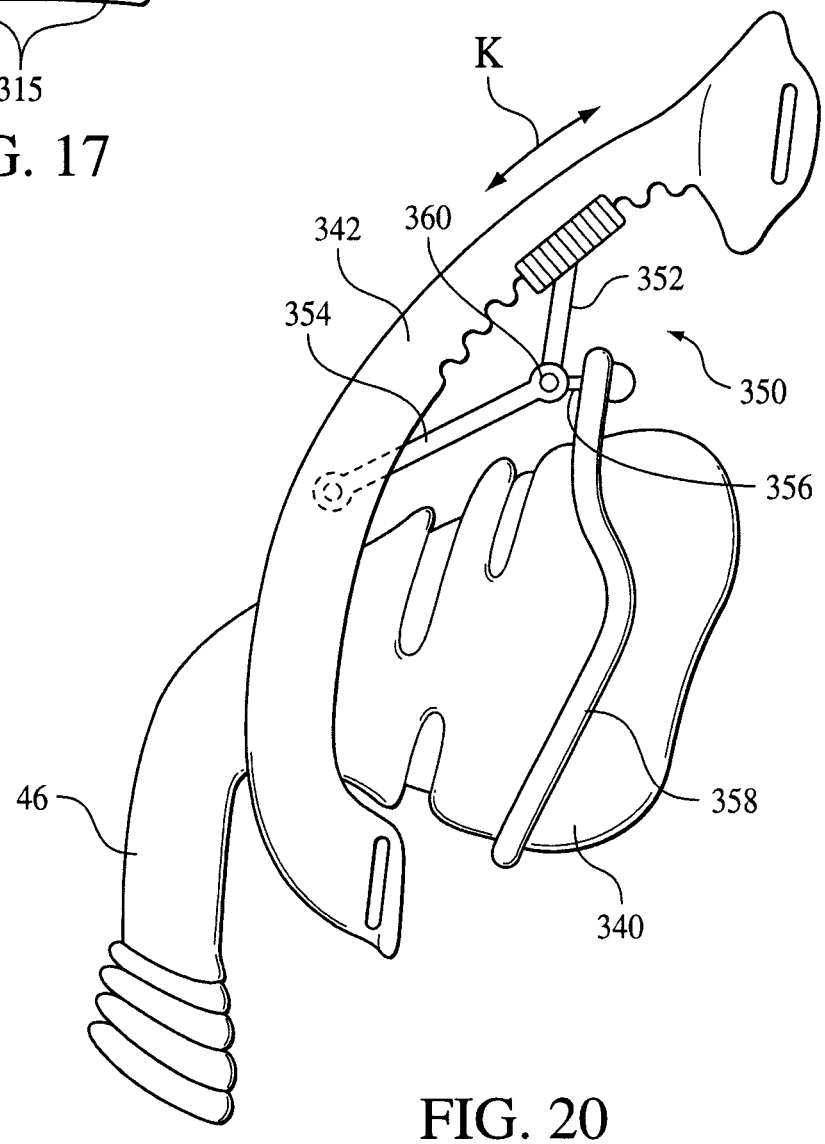
FIGS. 18-20 are side views of alternative embodiments of an adjustment mechanism that controls the position of the seal member relative to the faceplate.
Figure 19:
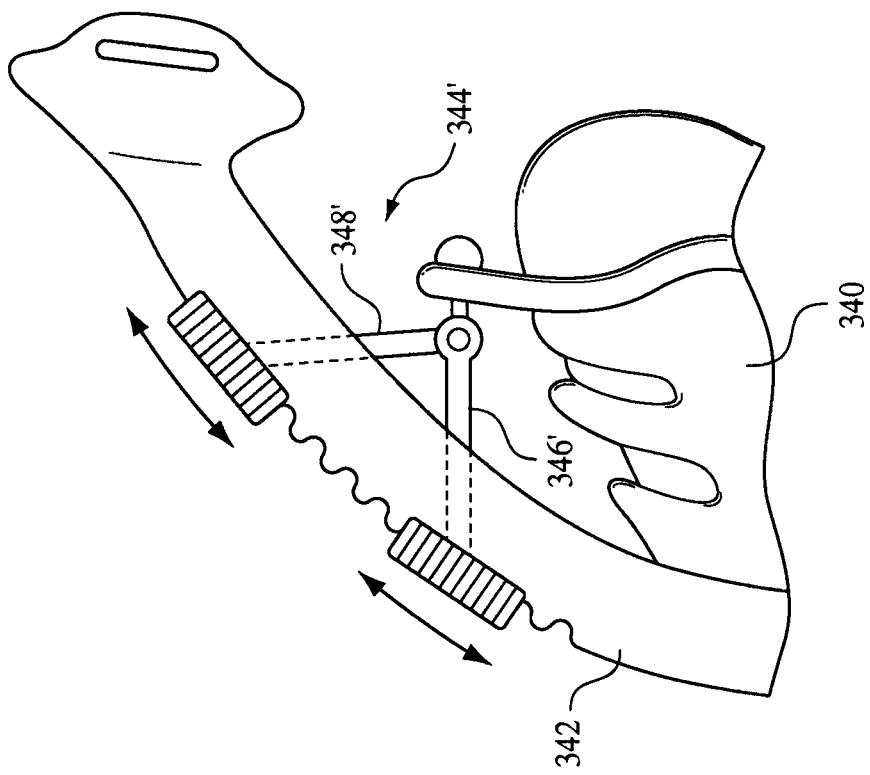
Figure 18:
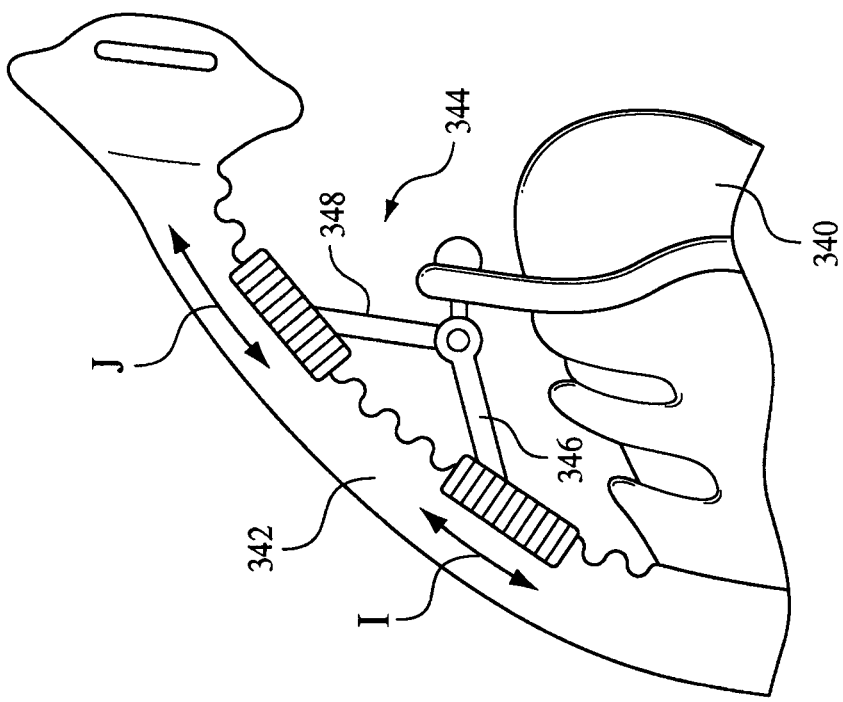

It can be appreciated that the present invention contemplates that the adjustment mechanism for controlling the position of the seal member relative to the face plate can have a wide varied of configurations. FIGS. 18-20 illustrate alternative exemplary embodiments for the adjustment mechanism that controls the position of a seal member 340 relative to a faceplate 342. In FIG. 18, an adjustment mechanism 344 is shown that includes a pair of linkages 346 and 348. The end of each linkage is coupled to faceplate 342 such that it is moveable along a portion of the faceplate, as indicated by arrows I and J. The ends of the linkages can be moved in discrete positions along the teeth provided on the faceplate to control the position of the patient contacting portion of the seal member. In the embodiment shown in FIG. 18, the linkages connect to a side of the faceplate proximate to the seal member. In the embodiment shown in FIG. 19, linkages 346' and 348' connect to a side of the faceplate opposite the seal member.

In FIG. 20, an adjustment mechanism 350 includes a pair of linkages 352 and 354, only one of which (linkage 352) is adjustably coupled to faceplate 342, as indicated by arrow K. Linkage 354 is rotatably coupled to the faceplate so that it can rotate as linkage 352 is moved. A third linkage 356 couples the other linkage to an attachment ring 358 in seal member 340. Linkages 352, 354, and 356 are rotatably coupled together at joint 360.

Figure 21:
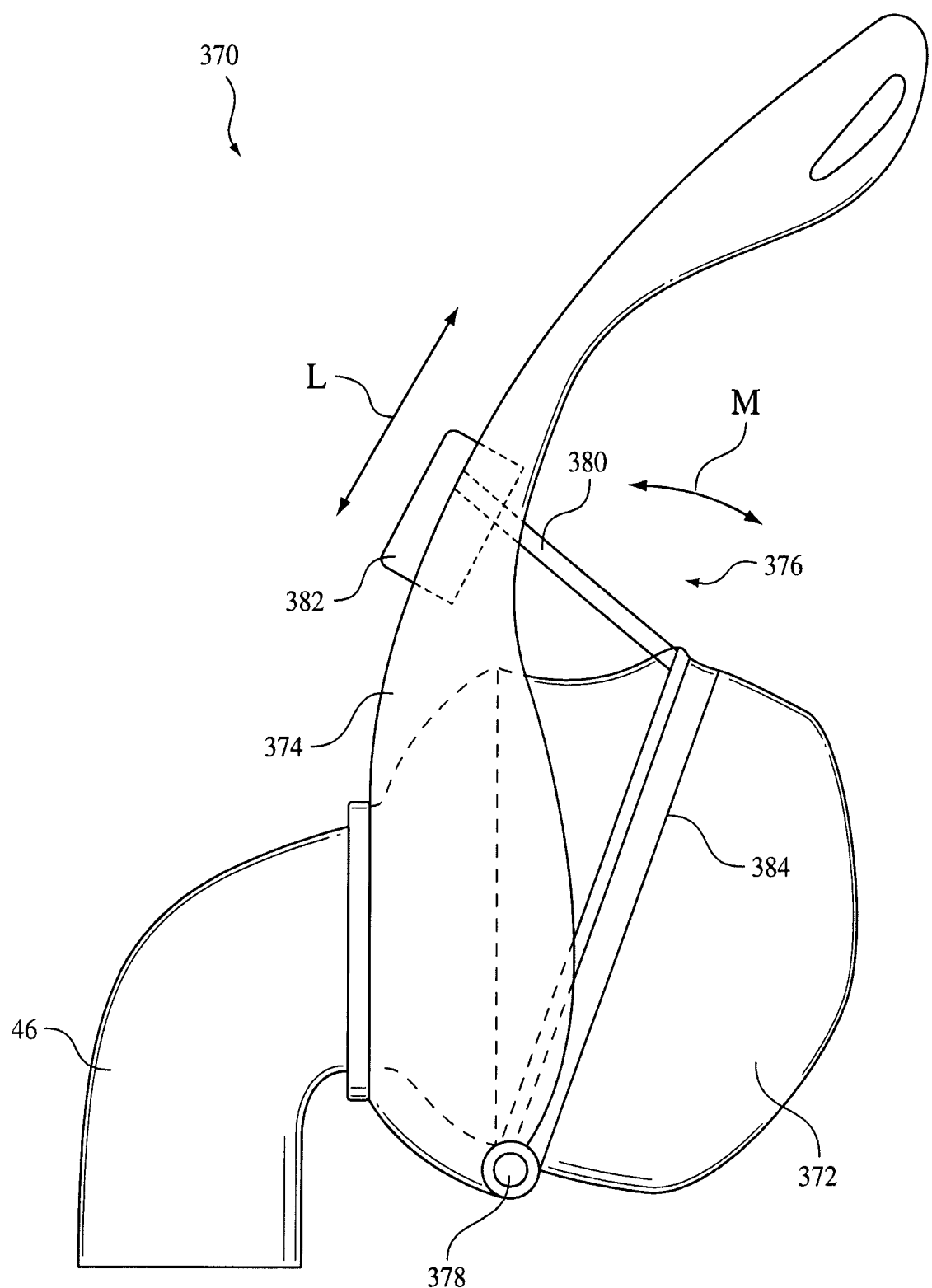
FIG. 21 is a side view of a fifth embodiment of a patient interface according to the principles of the present invention.

A fifth embodiment of a patient interface 370 according to the principles of the present invention is illustrated in FIG. 21. In this embodiment, a seal member 372 is coupled to a faceplate 374 such that one end of the seal member is rotatably attached to the faceplate and another end of the seal member is adjustably coupled to the faceplate via an adjustment mechanism 376. To rotatably attach the seal member to the faceplate a rotatable coupling 378 is provided at the lower portion of the patient interface.

Adjustment mechanism 376 includes a fixed length coupling member 380 and a moveable adjustment member 382 that is coupled to the faceplate and coupling member 380. Coupling member 380 is coupled between adjustment member 382 and seal member 372, and, in particular, an attachment ring 384, provided on the seal member. As a result, movement of adjustment member 382 along the faceplate, as indicated by arrow L, causes the upper portion of the seal member to move toward or away from the faceplate, as indicated by arrow M. However, the lower portion the seal member remains fixed to the lower portion of the faceplate so that the seal member rotates about and axis defined through rotatable coupling 378.

Figure 22:
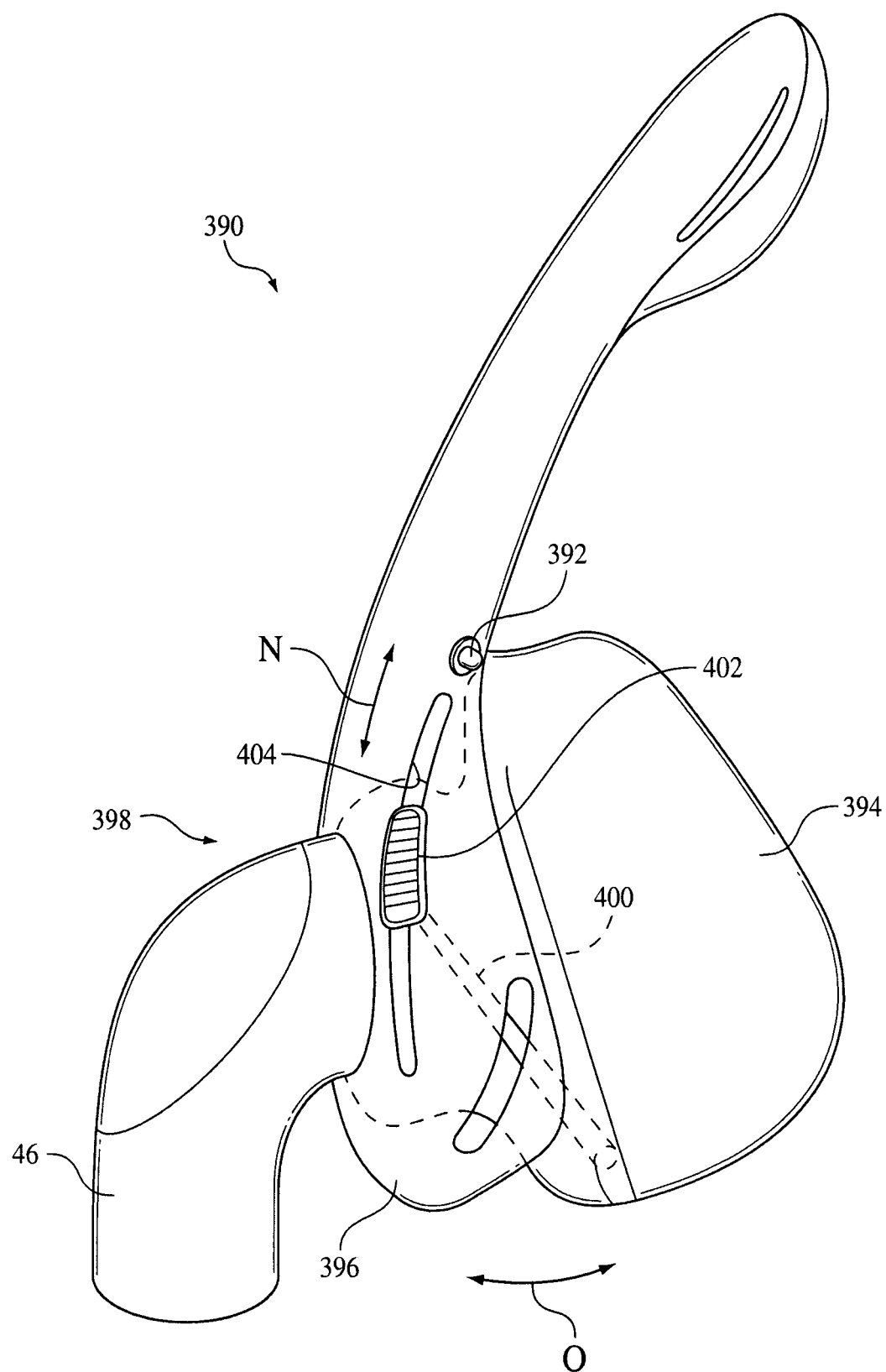
FIG. 22 is a side view of a sixth embodiment of a patient interface according to the principles of the present invention.

FIG. 22 illustrates a patient interface 390 that is generally similar to patient interface 370 of FIG. 21, except that it includes a rotatable coupling 392 between a seal member 394 and a faceplate 396 that is located at a lower portion of the patient interface. An adjustment mechanism 398 is provided to adjust the position of the patient contact portion of the seal member relative to the faceplate. In this embodiment, adjustment mechanism 398 includes a fixed length coupling member 400 and a moveable adjustment member 402 that is coupled to the faceplate and coupling member 400. Adjustment member 402 is moveable along a slot or track 404 defined in the faceplate, as indicated by arrow N. One end of coupling member 400 is rotatably attached to adjustment member 402 and another end is rotatably coupled to an attachment ring 406 of seal member 400. Movement of adjustment member 402 along slot 404 in the faceplate causes the lower portion of the seal member to move toward or away from the faceplate, as indicated by arrow O. However, the upper portion the seal member remains fixed to the upper portion of the faceplate so that the seal member rotates about and axis defined through rotatable coupling 392.

Figure 23:
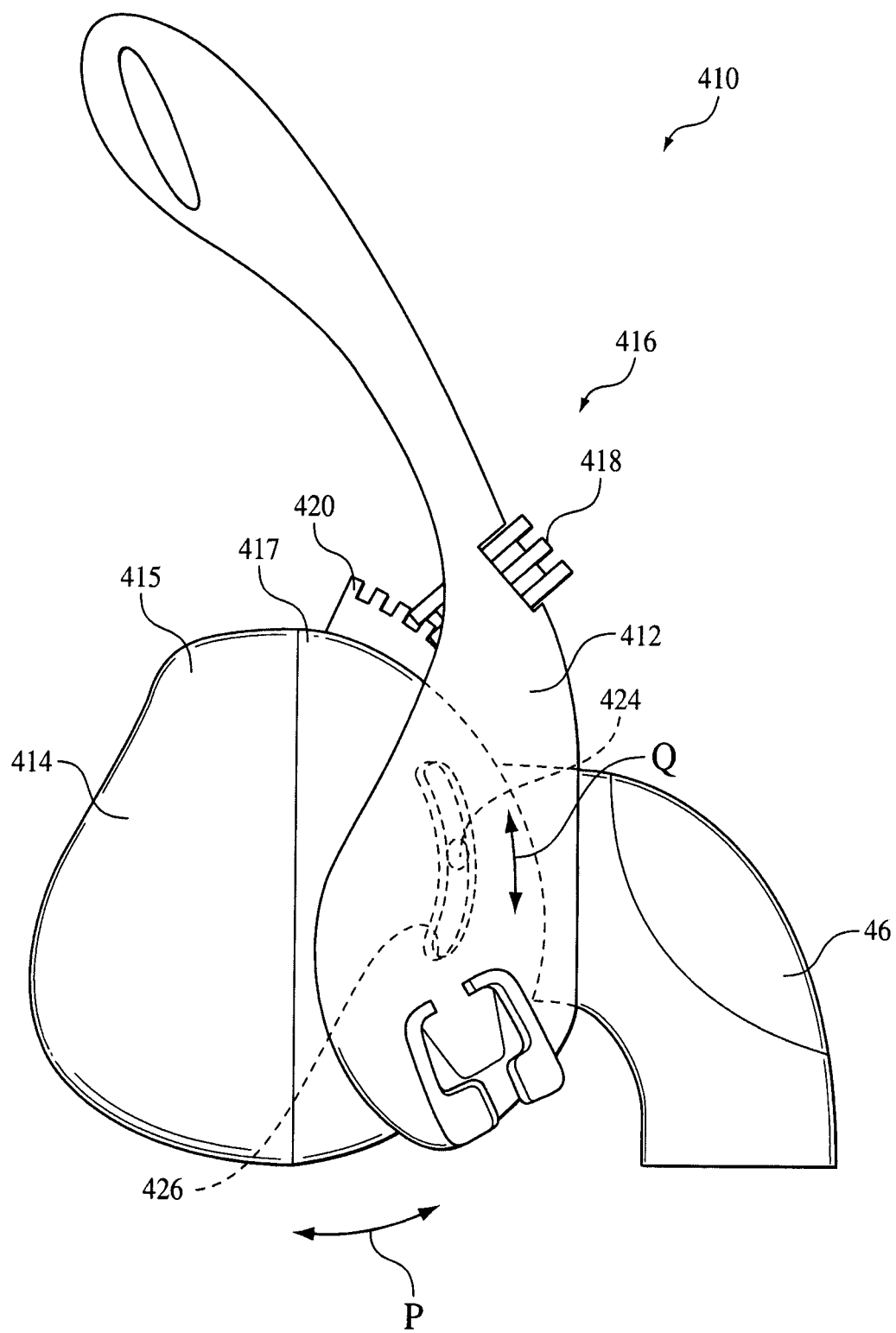
FIG. 23 is a side view of a seventh embodiment of a patient interface according to the principles of the present invention.

Yet another embodiment for the adjustment mechanism that controls the position of the seal member relative to the faceplate is discussed below with respect to the seventh embodiment of a patient interface 410 shown in FIGS. 23-24C. In this embodiment, patient interface 410 includes a faceplate 412, a seal member 414, and an adjustment mechanism 416 that controls the position of the seal member relative to the faceplate. Seal member 414 is defined by a cushion 415 and a rigid or semi-rigid support member 417 that is less flexible than the cushion. Adjustment mechanism 416 includes a screw 418, which is also referred to as a "thumb screw", that is attached to faceplate 412 and is rotated by the user. In an exemplary embodiment, screw 418 is mounted on a peg 419 that protrudes from the faceplate. See FIG. 25. Screw 418 engages teeth 420 provided on support member 417 of seal member 414 when the screw is rotated causing the seal member to move relative to the faceplate, as indicated by arrow P.

Figure 24C:
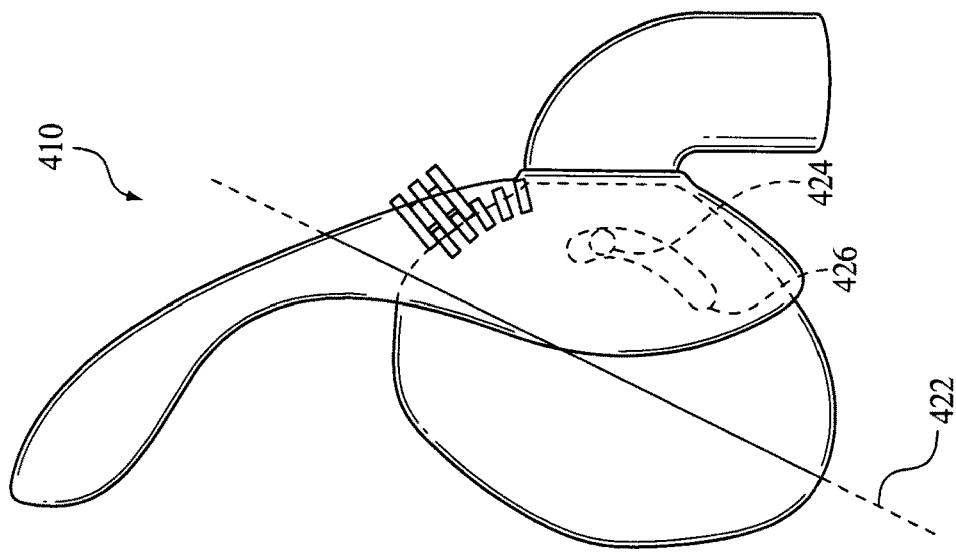
FIGS. 24A-24C are side views illustrating the adjustment of the seal member relative to the faceplate in the patient interface of FIG. 23.
Figure 24B:
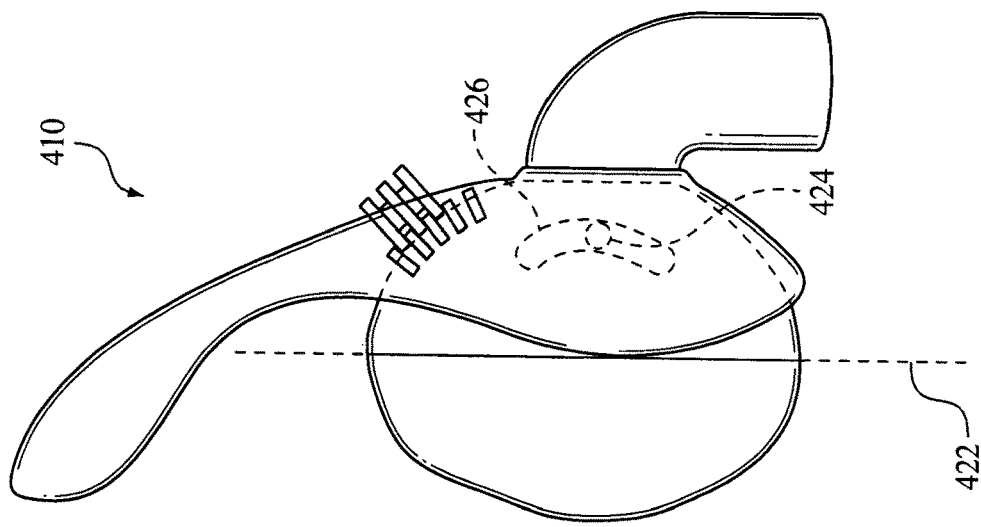
Figure 24A:
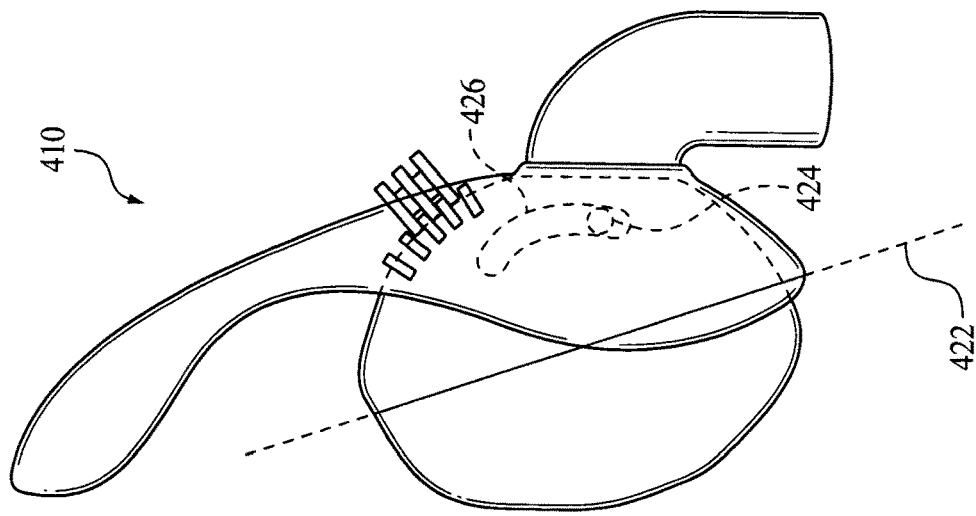

FIGS. 24A-24C are side views illustrating the adjustment of the seal member relative to the faceplate by adjustment mechanism 416. It can be appreciated from viewing these figures that rotation of the screw causes it to move along the teeth provided on the seal member, thereby changing the angle between a plane 422, which is defined by the seal member, and the faceplate. This embodiment allows the seal member to be placed in an infinite number of positions relative to the faceplate over the range of angles possible using adjustment mechanism 416. The present invention contemplates coupling the interior of the seal member with the patient circuit via a flexible collar 442.

To maintain the seal member in alignment with the faceplate, patient interface 410 includes a guide member 424 provided on faceplate 412, and a corresponding slot or track 426 provided in seal member 414. Of course, the present invention contemplates that track 426 can be disposed on the faceplate and the guide member can be provided on the seal member. It should also be noted that a track and guide member can be provided on each side of the mask, where only one side is shown in the illustrated embodiments. The guide member and track are configured such that the guide member moves along the track, as indicated by arrow Q, during adjustment of the position of the seal member relative to the faceplate. It should be further understood that the location, size, and configuration the track and guide member can be varied so that the way in which the seal member moves relative to the track can be controlled. For example, the present invention contemplates that the track can have an wavy configuration and/or can be wider in certain regions to allow for some degree of freedom of movement of the seal member relative to the faceplate.

Figure 25:
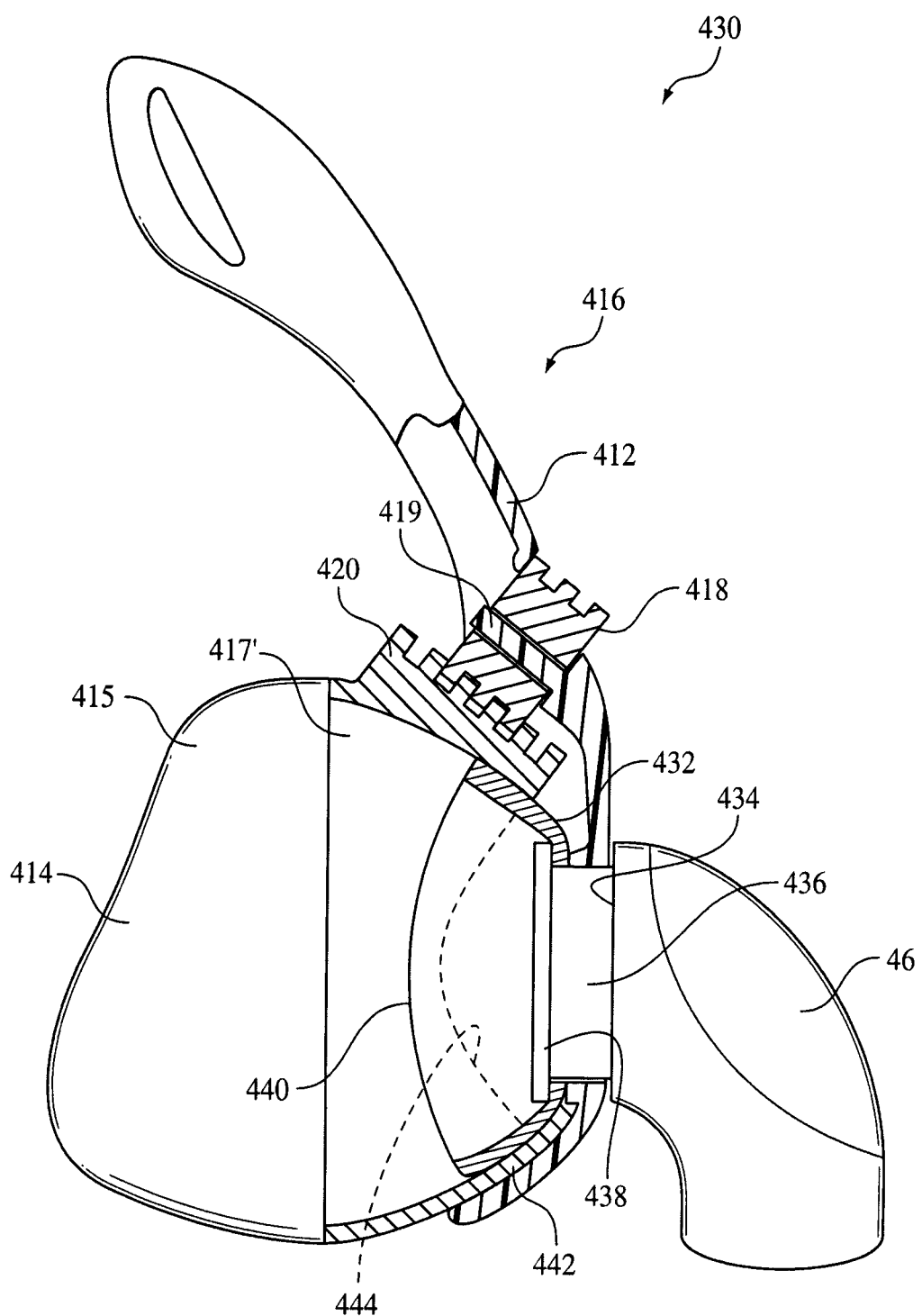
FIG. 25 is a side, partial sectional, view of an eighth embodiment of a patient interface according to the principles of the present invention.
Figure 26:
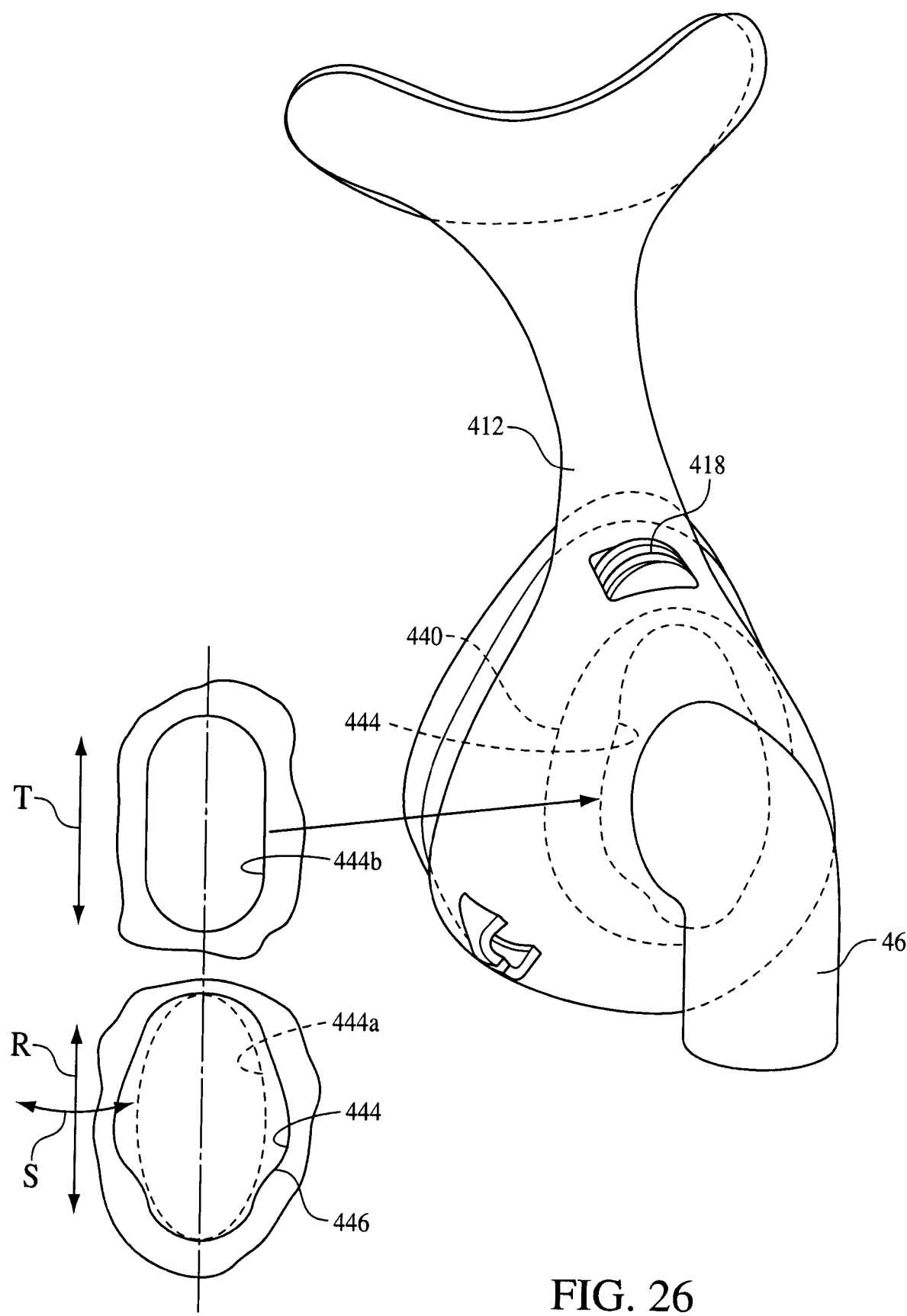
FIG. 26 is a perspective view of alternative configurations for the seal member mount in the patient interface of FIG. 23.

FIGS. 25 and 26 illustrates an eighth embodiment of a patient interface 430 according to the principles of the present invention. Patient interface 430 is generally similar to patient interface 410 of FIGS. 23-24C. However, patient interface 430 includes a technique for coupling seal member 414 to faceplate 412 that is different from the flexible collar and the guide member and track configuration of patient interface 410 in the previous embodiment. In this embodiment, a collar 432 is coupled in a groove 434 provided at an end portion 436 of coupling member 46. A lip 438 maintains collar in an engaged relation with the coupling member. Collar 432 flares outward from the coupling member and terminates in a peripheral edge 440.

A peripheral edge portion 442 of support member 417' defines an opening 444 that surrounds the coupling between collar 432/faceplate 412 and coupling member 46. Thus, the peripheral edge portion of the support member is disposed between the collar and the faceplate. As seal member 414 moves relative to the faceplate, support member 417' moves relative to collar 432. The shape of opening 444 defines the degree of movement that is possible between the seal member and the faceplate.

In one embodiment, opening 444 has an elliptical shape with a widened portion 446. This configuration allows the seal member to mover in a vertical direction relative to the faceplate, as indicated by arrow R, and in a horizontal direction, as indicated by arrow S. The degree of freedom of movement is controlled by changing the dimensions of opening 444. For example, opening 444a is shown in FIG. 26 that is smaller than opening 444. Thus, opening 444a provides less freedom of movement between the seal member and the faceplate. If it is desired to limit the movement of the seal member relative to the faceplate to one dimension, such as in a vertical direction as indicated by arrow T, the opening can be made in the form of a slot as shown by opening 444c. It can be appreciated that the present invention contemplates a wide variety of configurations for opening 444.

Figure 27:
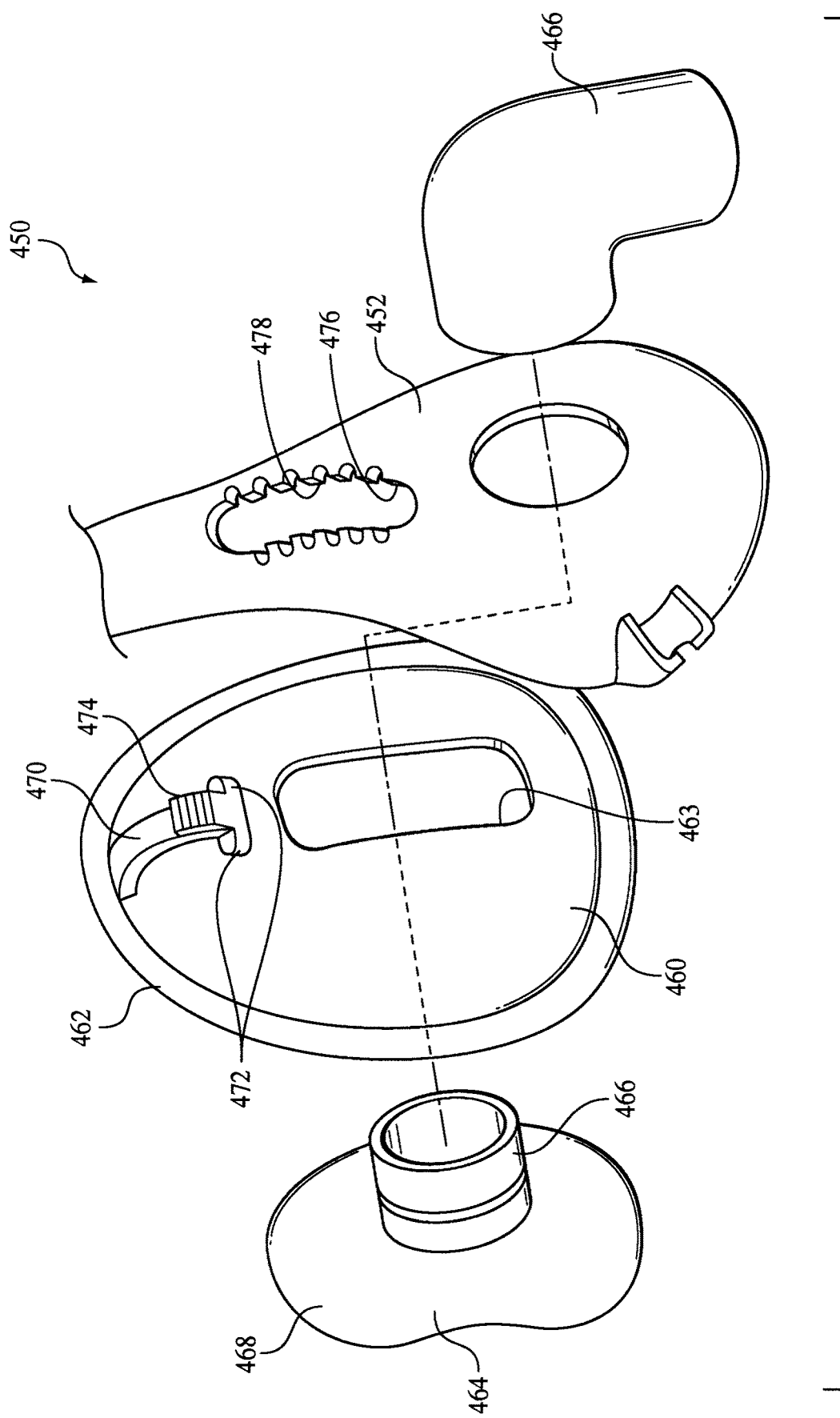
FIG. 27 is an exploded view of a ninth embodiment of an adjustment mechanism according to the principles of the present invention.
Figure 28:
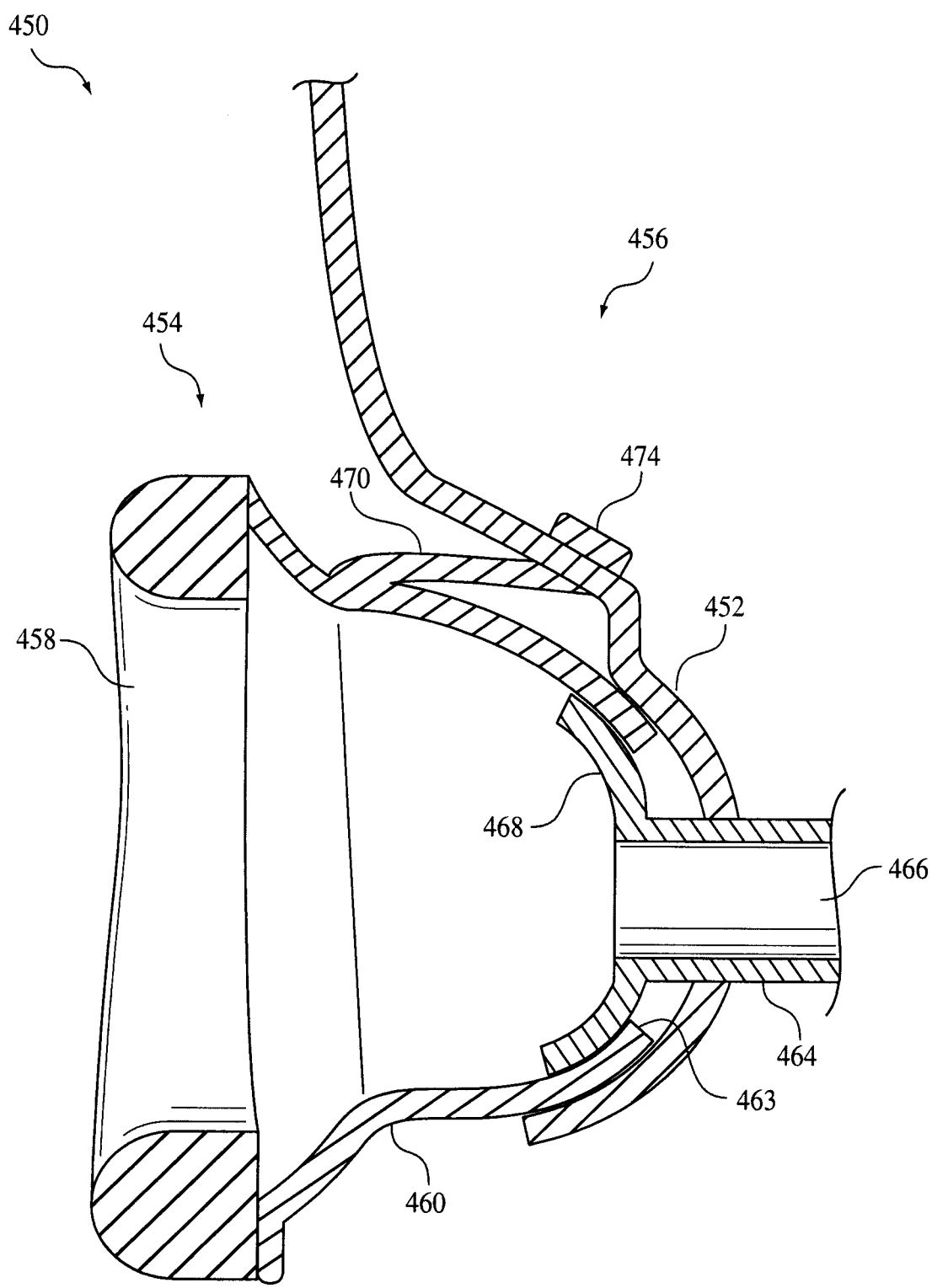
FIG. 28 is a side sectional view of a patient interface including the adjustment mechanism of FIG. 27.

FIGS. 27 and 28 illustrate a ninth embodiment of a patient interface 450 having yet another configuration for an adjustment mechanism 456 that couples a seal member 454 to a faceplate 452. It should be noted that the forehead support portion of the patient interface is omitted from these figures. Seal member 454 includes a cushion 458 and a support member 460 having a peripheral portion 462 to which the cushion is mounted. An opening 463 is defined in support member 460.

A collar 464, which includes a neck portion 466 and a flange 468 couples the seal member to the faceplate. As in the embodiment of FIG. 25, a peripheral portion of portion of support member 460 is sandwiched between a portion of flange 468 and a portion of the faceplate. Neck portion 466 passes through opening 463. As the seal member is moved by adjustment mechanism 456, support member 460 moves relative to collar 464 and faceplate 452. Again, the shape of opening 463 controls how the seal member moves relative to the faceplate.

In this embodiment, adjustment mechanism 456 includes a manually deflectable arm 470 that extends from support portion 460. Contacting members 472 and a protrusion 474 are provided at the end of the arm. Adjustment mechanism 456 also includes a slot 476 provided on faceplate 452. A plurality of notches or detents 478 are provided on the sides of slot 476. When assembled, protrusion 474 extends above the exposed surface of the faceplate and contacting members 472 engage on pair of notches 478. To change the position of the seal member relative to the faceplate, the user depresses protrusion 474 to disengage the contacting members from the notches and slides the arm up or down the slot. The user then releases the arm, which is then biased again into engagement between the contacting member and the notches to maintain the seal member in its new position.

Figure 29:
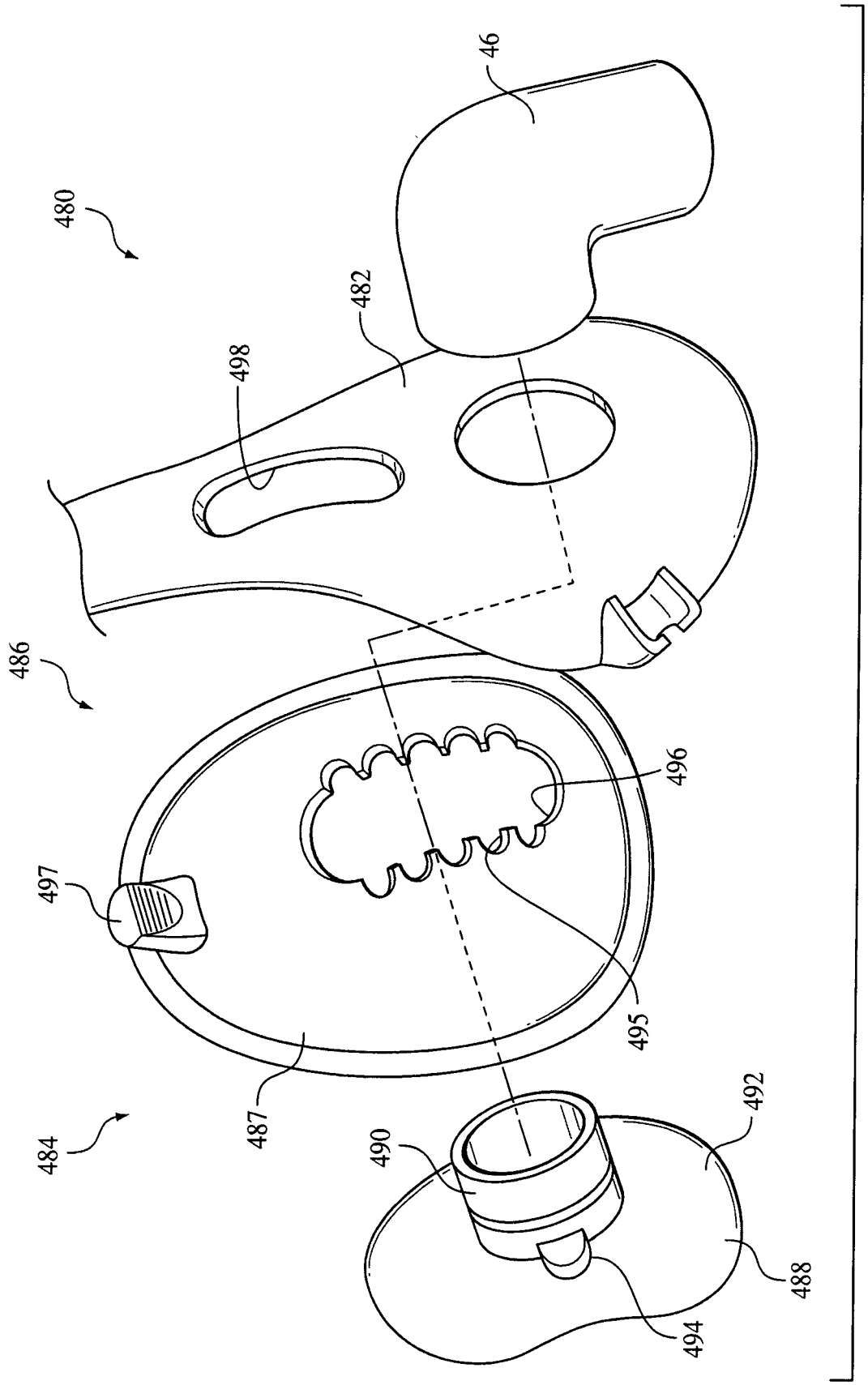
FIG. 29 is an exploded view of a tenth embodiment of an adjustment mechanism according to the principles of the present invention.

A tenth embodiment of patient interface 480 is illustrated in FIG. 29, which is an exploded view the patient interface showing a faceplate 482 and a seal member 484. The seal member includes a cushion (not shown) mounted onto a support member 487. At least a portion of an adjustment mechanism, generally indicated at 486, is incorporated into the coupling between the seal member and the patient interface where the seal member communicates with coupling member 46. As in the previous embodiment, a collar 488, which includes a neck portion 490 and a flange 492 couples the seal member to the faceplate. Unlike the previous embodiment, collar 488 is used to set the position of the seal member relative to the face plate, and, thus, constitutes a portion of adjustment mechanism 486.

Neck portion 490 of collar 488 includes a pair of contacting members 494 (only one of which is shown) each of which is provided on one side of the neck portion. Contact members 494 are sized and configured to engage notches 495 provided on the sides of a slot 496. Support member 487 of seal member 484 moves relative to faceplate 482 and collar 488 to change the position of the patient contacting portion of the seal member relative to the faceplate. The engagement between notches 495 and contact members 494 maintains the position of the seal member relative to the faceplate. To facilitate movement of the seal member relative to the faceplate, a protrusion 497 is provided extending from support member 487, and a slot 498 is provided in the faceplate. Protrusion 497 extends through slot 498 so that the user can grasp or push the protrusion to change the position of the seal member relative to the faceplate.

Figure 30:
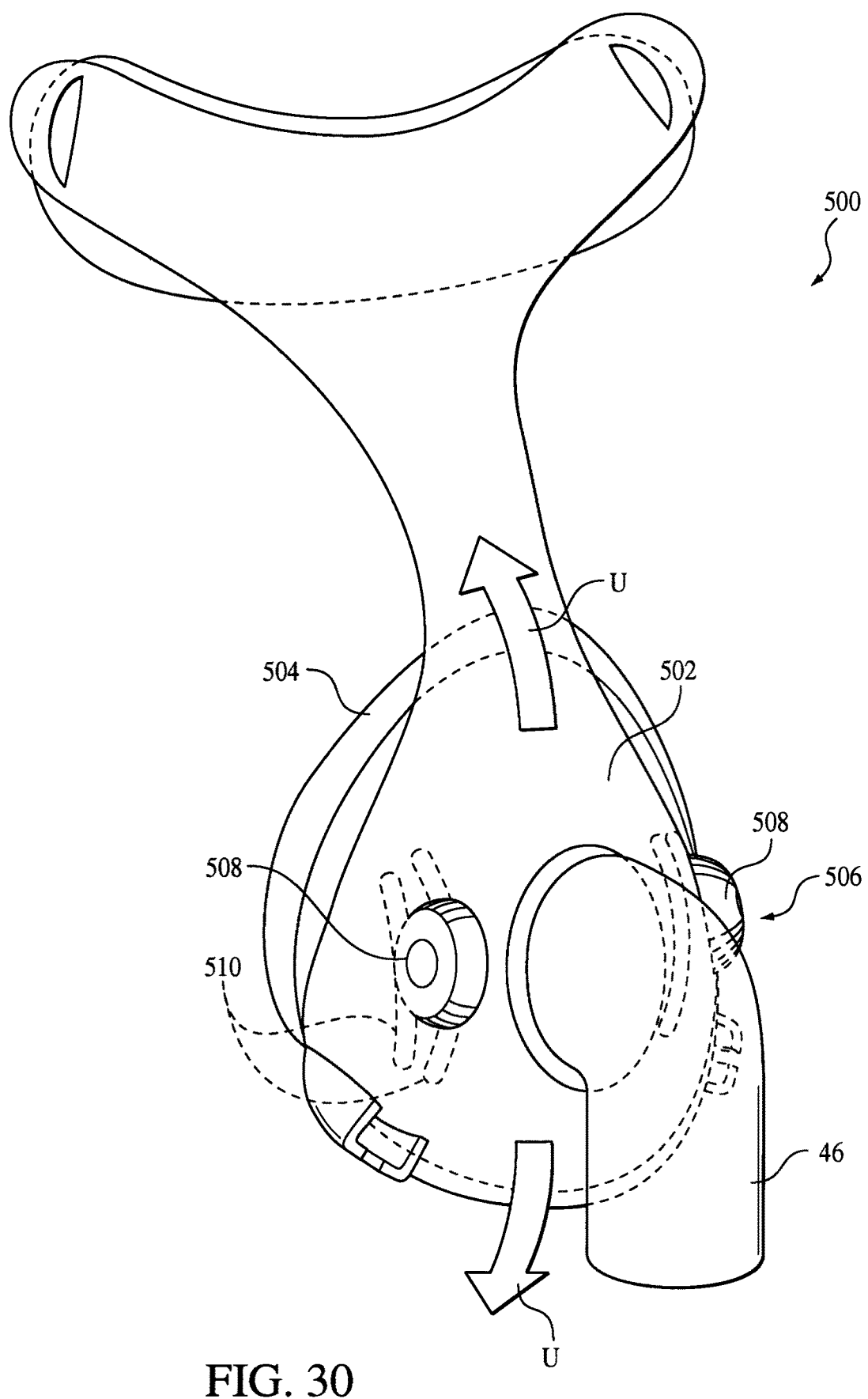
FIG. 30 is a front perspective view of an eleventh embodiment of a patient interface according to the principles of the present invention.

FIG. 30 illustrates an eleventh embodiment of a patient interface 500 according to the principles of the present invention. Patient interface 500 includes a faceplate 502, a seal member 504, and an adjustment mechanism, generally indicated at 506. In this embodiment, adjustment mechanism 506 includes a pair of manually actuated knobs or wheels 508 disposed on either side of the faceplate and rotatably coupled to the faceplate. Knobs 508 engage seal member which is flexibly coupled to the faceplate and coupling member 46 such that rotating the knobs moves the seal member relative to the faceplate, as indicated by arrows U. Friction or a locking mechanism (not shown) can be used to prevent movement of the knobs.

The present invention also contemplates that knobs 508 only engage the seal member when it is desired to change the position of the seal member relative to the faceplate. At all other times, the knobs are disengaged from the faceplate. In an exemplary embodiment of the present invention, this is accomplished by providing engagement tracks 510 on seal member 504. Knobs 504 are actuated to engage tracks 510 by moving them in a lateral direction, for example by squeezing the knobs to move them toward the center of the faceplate. A biasing mechanism, such as a spring, causes the knobs to disengage from the tracks once the squeezing for is released. In the illustrated embodiment, multiple tracks 510 are provided on the seal member to ensure that the knobs engage the tracks to move the seal member.

Figure 31:
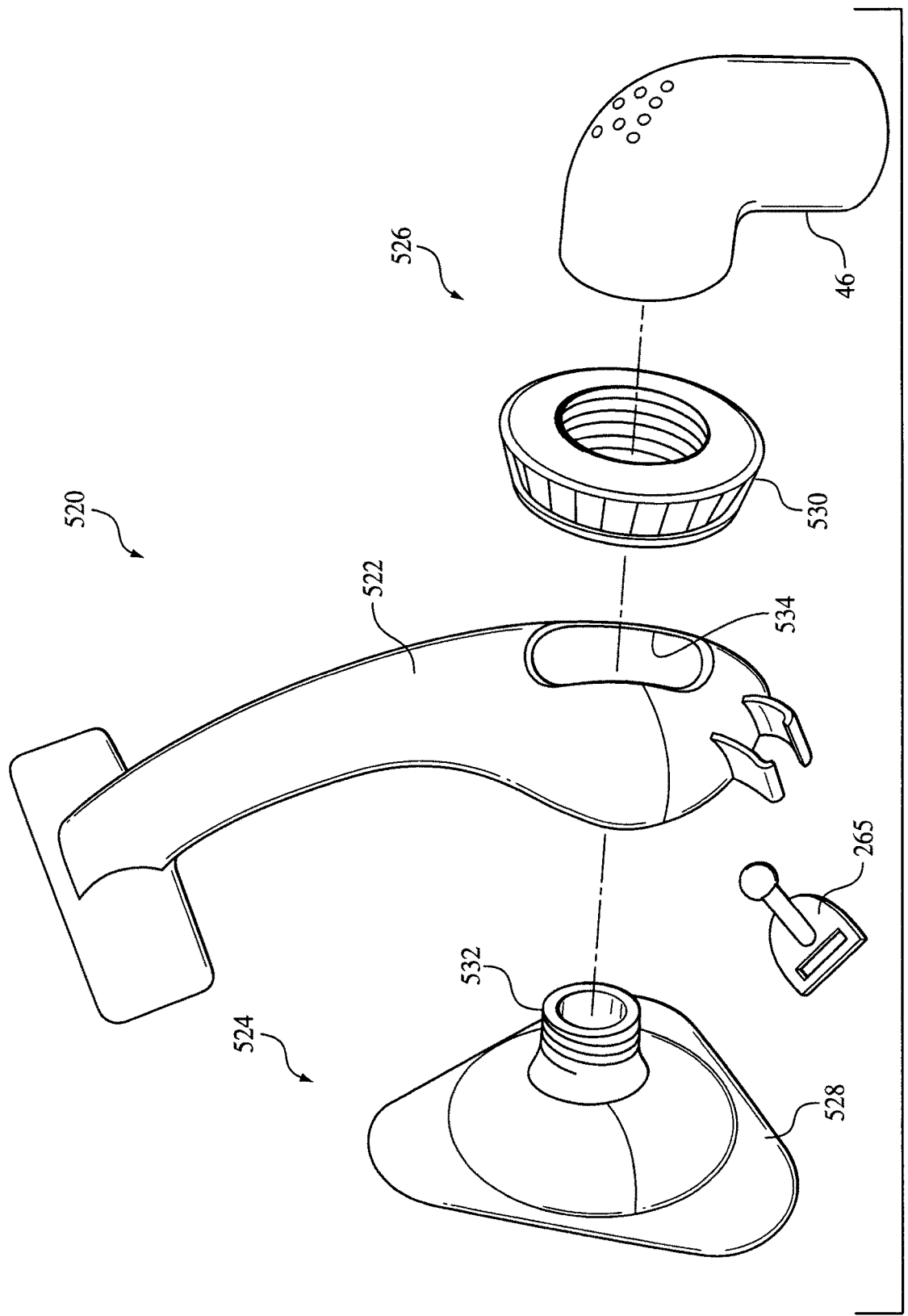
FIG. 31 is an exploded view of a twelfth embodiment of a patient interface according to the principles of the present invention.

FIG. 31 illustrates a twelfth embodiment of a patient interface 520 according to the principles of the present invention. Patient interface 520 includes a faceplate 522, a seal member 524, and an adjustment mechanism, generally indicated at 526. It should be noted that seal member 524, as shown, only includes a support member 528. The patient contacting cushion that attaches to support member 528 is not shown. It should be noted that the cushion can be attached to support member 528 such that the cushion and support member define a unitary structure. The present invention also contemplates using the support member as collar 432 cushion be In this embodiment, adjustment mechanism 526 includes a lock nut 530 that attaches to a neck portion 532 of support member 528. Threads on the lock nut and the neck portion attach these components together. However, other techniques are contemplated by the present invention. Neck portion 532 passes through an orifice 534 defined in faceplate 502 and attaches to the lock nut. It is to be understood that coupling member 46 is attached to the faceplate or the lock nut. It should also be noted that the components of patient interface 520 are not drawn to scale.

Figure 32:
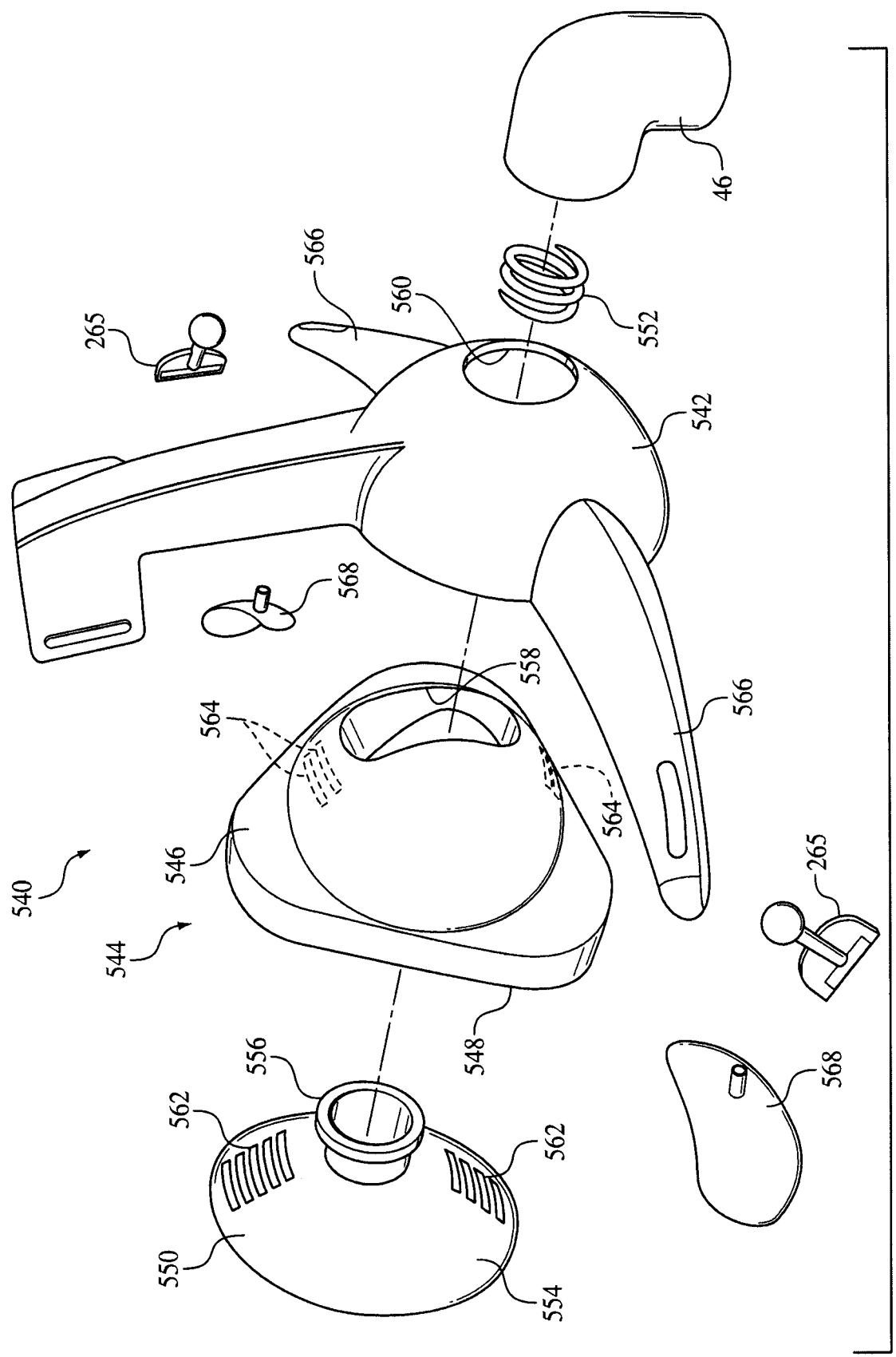
FIG. 32 is an exploded view of a thirteenth embodiment of a patient interface according to the principles of the present invention.

FIG. 32 is an exploded view of a thirteenth embodiment of a patient interface 540 according to the principles of the present invention. Patient interface 540 includes a faceplate 542 and a seal member 544. It should be noted that seal member 544, as shown, only includes a support member 546. The patient contacting cushion that attaches to support member 546 is not shown. In this embodiment, the cushion attaches to an end portion 548 of support member 546.

A collar 550 is seated in support member 546 and secures the support member against faceplate 542 in a manner similar to that of collar 432 in FIG. 25. A biasing mechanism in the form a spring 552 urges a flange 554 of collar 550 toward the inner surface of the faceplate. This can be accomplished, for example, by using the spring to "push" the faceplate toward the flange of the collar or by having the spring "pull" the collar toward the faceplate. Collar 554 remains fixed in position relative to faceplate 542 and coupling member 46. However, seal support member 546 is moveable relative to the these components. A neck portion 556 of collar 550 is inserted through an orifice 558 of support member 546 and an orifice 560 of faceplate 542 and is operatively coupled coupling member 46.

A plurality of teeth 562 are provided on a surface of the collar, and corresponding teeth engaging components 564 are provided on a surface of seal support member 546 that confronts the teeth carrying surface of the collar. Teeth 562 and teeth engaging components 564 cooperate to provide discrete positions for the seal member relative to the faceplate. To change the position of the seal member relative to the faceplate, the user pulls the seal member slightly away from the faceplate against the bias force of spring 552 far enough to disengage the teeth 562 from teeth engaging components 564. The user then moves the seal member to the new position and releases the seal member, allowing the teeth to reengage the teeth engaging components at the new position, thereby preventing any unwanted movement between the seal member and the faceplate.

It is to be understood that the present invention contemplates that the teeth and the teeth engaging components can have a variety of configurations and can be provided at a variety of locations on the collar and the seal support member. For example, a tongue and groove configuration can be used. In addition, the location of the teeth and the teeth engaging components can be reversed so that the teeth are provided on the seal support member.

In this embodiment, faceplate 542 has a pair of lateral arms 566 that extend from each side of a central portion of the faceplate. The lateral arms are configured and arranged so to be positioned over the user's cheeks when the patient interface is being worn by the user. Pads 568 are connected to the lateral arms to contact the surface of the user.

Figure 33:
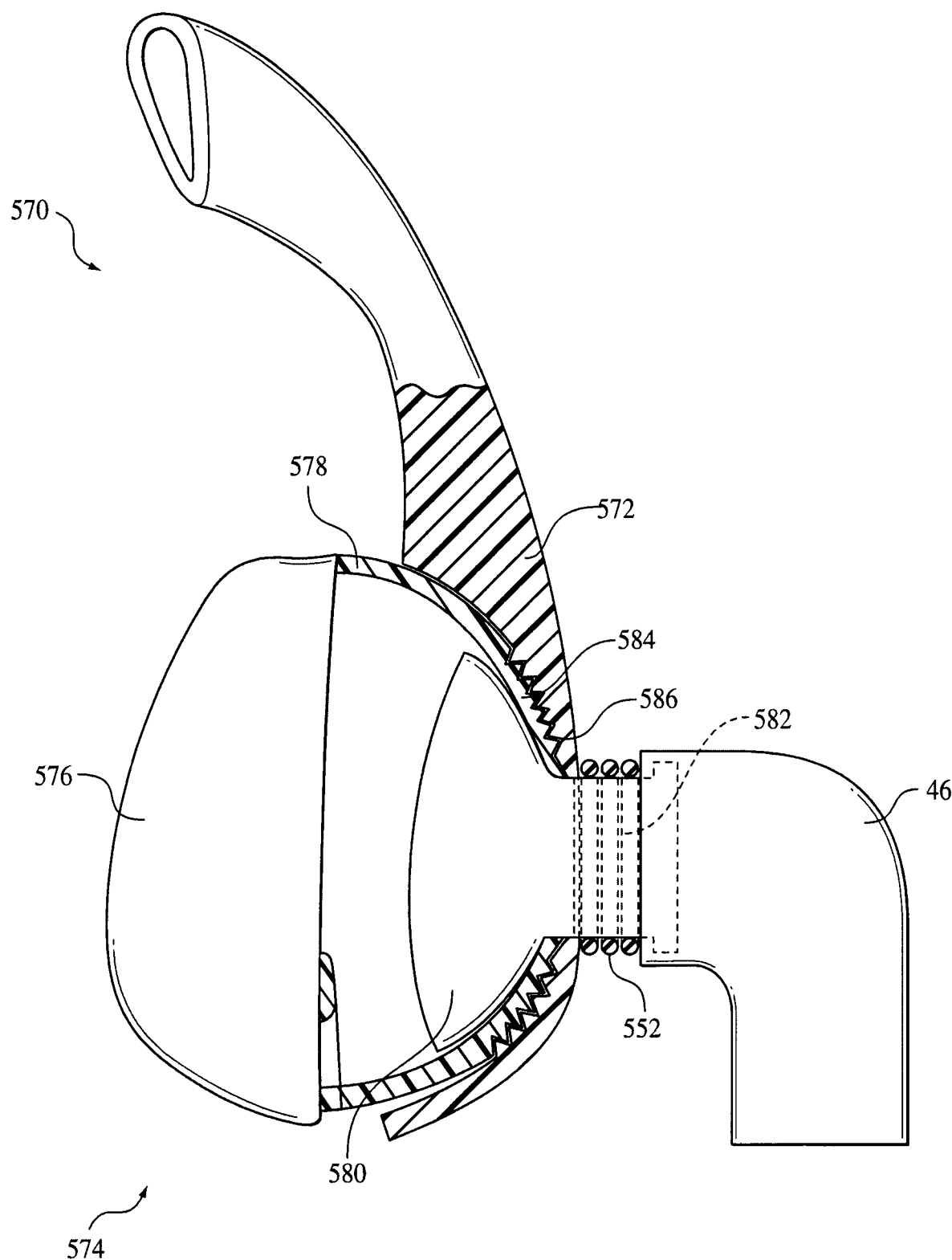
FIG. 33 is a side view, partially in section, of a fourteenth embodiment of a patient interface according to the principles of the present invention.

FIG. 33 is a side view, partially in section, of a fourteenth embodiment of a patient interface 570 according to the principles of the present invention. Patient interface 570 includes a faceplate 572 and a seal member 574. Seal member 574 includes a cushion 576 and a seal support member 578. The adjustment mechanism by which the seal member is adjustably relative to the faceplate is generally similar to that used in patient interface 540 of FIG. 32. Namely, seal support member 578 is secured between a collar 580 and the faceplate. A spring 552, which is secured around a neck portion 582 of collar 580, biases the collar and faceplate against one another to hold the seal support member in place. The main functional difference resides in the location of the teeth that are used maintain the seal member in a fixed position relative to the faceplate.

In patient interface 570 of FIG. 33, a first group of teeth 584 are provided on surface of seal support member 578 and a second group of teeth 586 are provided on an interior surface of faceplate 572. Teeth 584 and 586 selectively engage one another to hold the seal member in position relative to the faceplate. Unlike the previous embodiment, the surface of the collar does not include any mechanism, such as teeth, for securing the seal member in place. It is to be understood that teeth 584 and 584 can have a variety of configures, and need not be "teeth". Rather, other structures such as a tongue and groove, or a friction surface can also be used to keep the components of the patient interface from moving until manually actuated by the user.

Figure 34:
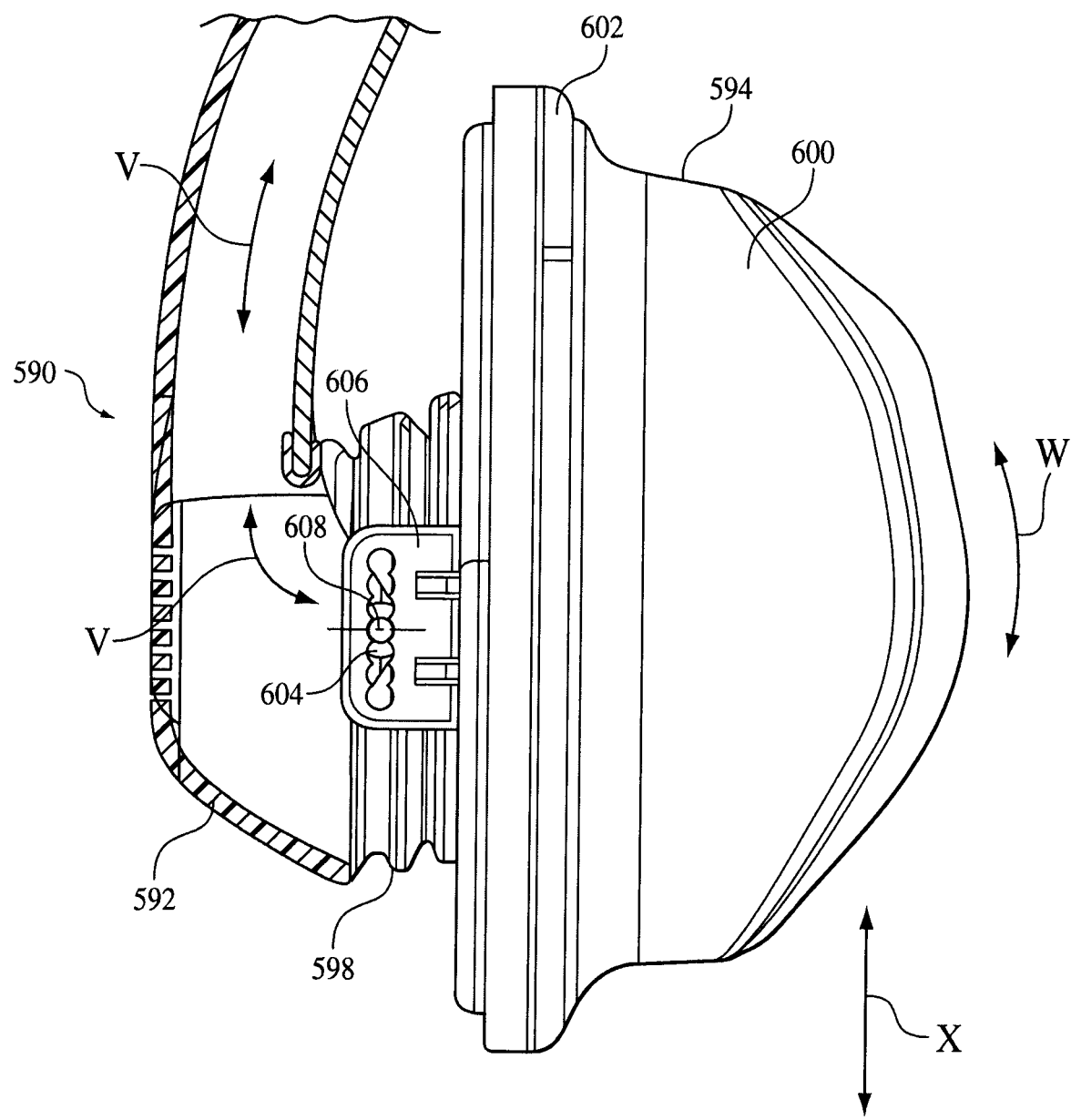
FIG. 34 is a side sectional view of a portion of a patient interface according to a fifteenth embodiment of the present invention.

FIG. 34 is a side sectional view of a portion of a further embodiment of patient interface 590 according to a fifteenth embodiment of the present invention. This embodiment is provided to illustrate alternative configurations for coupling a seal member 594 to a faceplate 592 and for communicating a flow of gas to the interior of the seal member. It should be noted that this figure does not show an structure for controlling the position of the seal member relative to the faceplate, but any of the techniques described herein can be used for that purpose. This figure also does not show the forehead support portion of the patient interface device. It is to be understood that any configuration for the forehead support, or the forehead support can be eliminated entirely.

In this embodiment, gas flow from the patient circuit is communicated to a forehead arm 596, which has a hollow interior, so that the gas flow passes through the forehead arm, as indicated by arrows V. The hollow interior of forehead arm 596 communicates with the interior of seal member 594 via a flexible collar 598. Seal member 594 includes a cushion 600 and a seal support member 602. One end of flexible collar 598 is coupled to faceplate 592 and another end is coupled to support member 602.

Another feature of patient interface 590 is the ability to control the position of the seal member relative to the faceplate in a vertical direction. That is, the seal member can be moved in a vertical direction, as indicate by arrow W and set in one of a plurality of discrete locations relative to the faceplate. This is accomplished by providing a slot 604 having a plurality of notches in a support member 606, which is attached to and extends from seal support member 602. A coupling member 608 is configured to be selectively disposed on one of the notches in slot 604. Coupling member 608 is rotatable within each notch so that the angle between a planed defined by the faceplate and a plane defined by the seal member can be changed, as indicated by arrow X.

Figure 35:
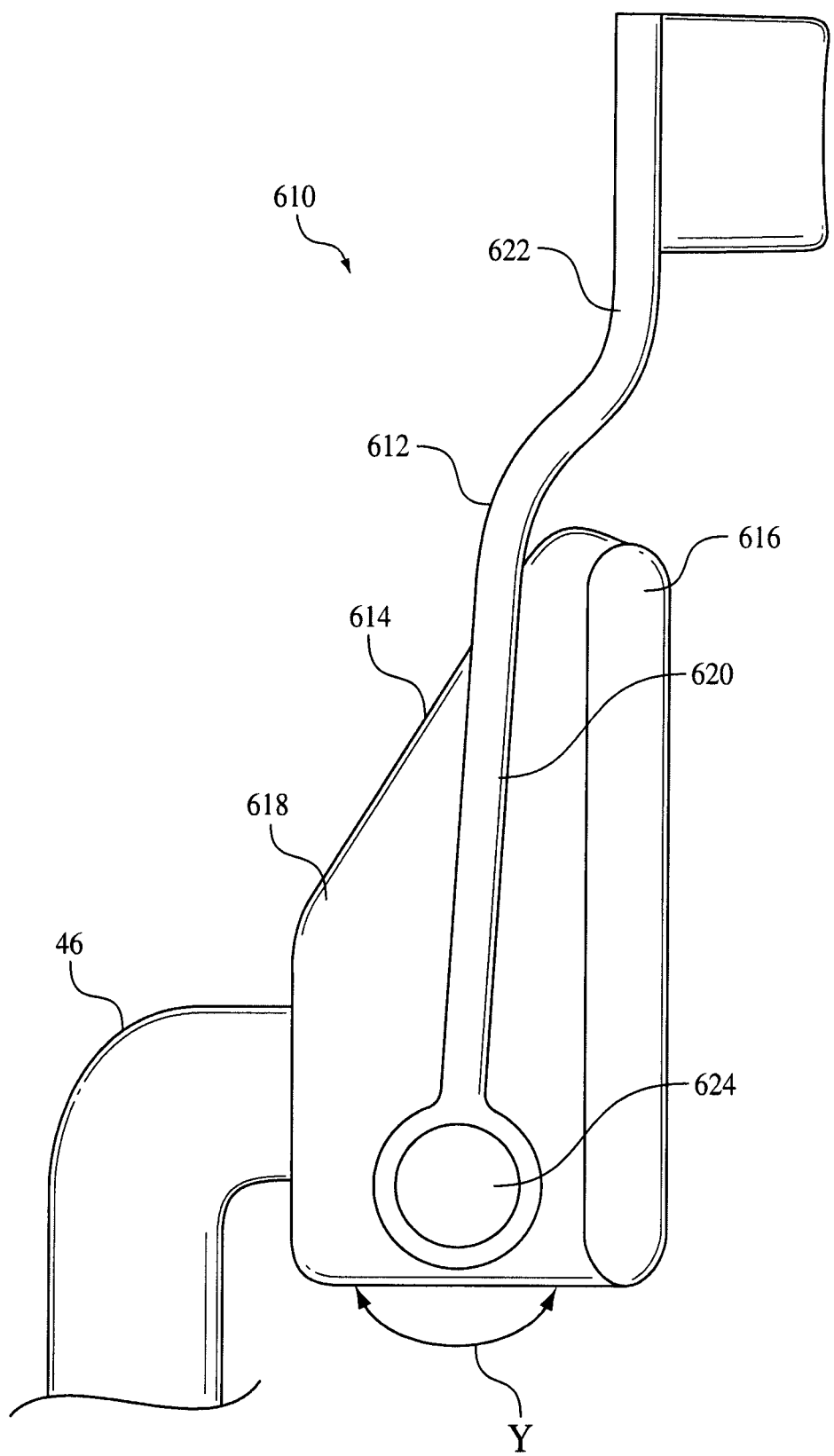
FIG. 35 is a side view of a sixteenth embodiment of a patient interface according to the principles of the present invention.
Figure 36:
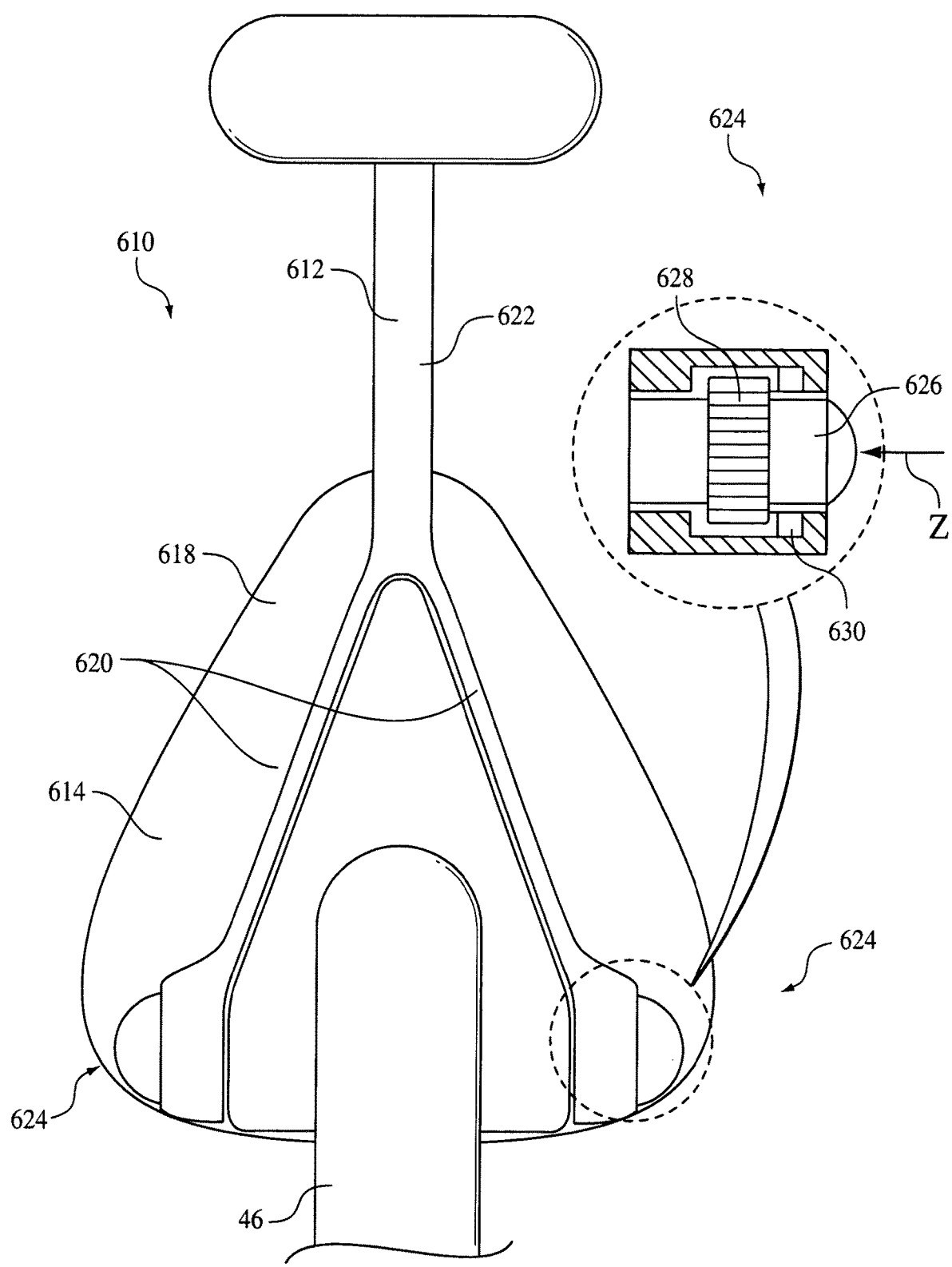
FIG. 36 is a front view of the patient interface of FIG. 35 including a detailed view of an adjustment mechanism used therein.

A sixteenth embodiment of a patient interface 610 according to the principles of the present invention is illustrated in FIGS. 35 and 36. Patient interface 610 includes a faceplate 612 and a seal member 614. In this embodiment, faceplate 612 is relatively small and is little more than a frame that support the seal member. Seal member 614 includes a cushion 616 and a seal support member 618. Faceplate 612 includes a pair of arm 620 that diverge from a forehead arm 622 and travel along opposite sides of seal support member 618. The ends of arms 620 are coupled to seal member 614 via an adjustment mechanism 624, which allows the user to set the position of the seal member relative to the faceplate. That is, adjustment mechanism 624 allows the seal member to rotate relative to the faceplate, as indicated by arrow Y, and allows the user lock the seal member at one of a plurality of discrete positions relative to the faceplate. The axis of rotation is defined through adjustment mechanisms 624.

In the illustrated exemplary embodiment, adjustment mechanism 624 is a push-button, ratchet mechanism that includes a spring-loaded button 626 having a plurality of teeth 628. When depressed, as indicated by arrow Z, teeth 628 are disengaged from a corresponding locking member 630 so that the seal member can be rotated relative to the faceplate. When released, the teeth engage the locking members preventing movement of the seal member relative to the faceplate.

Figure 37:
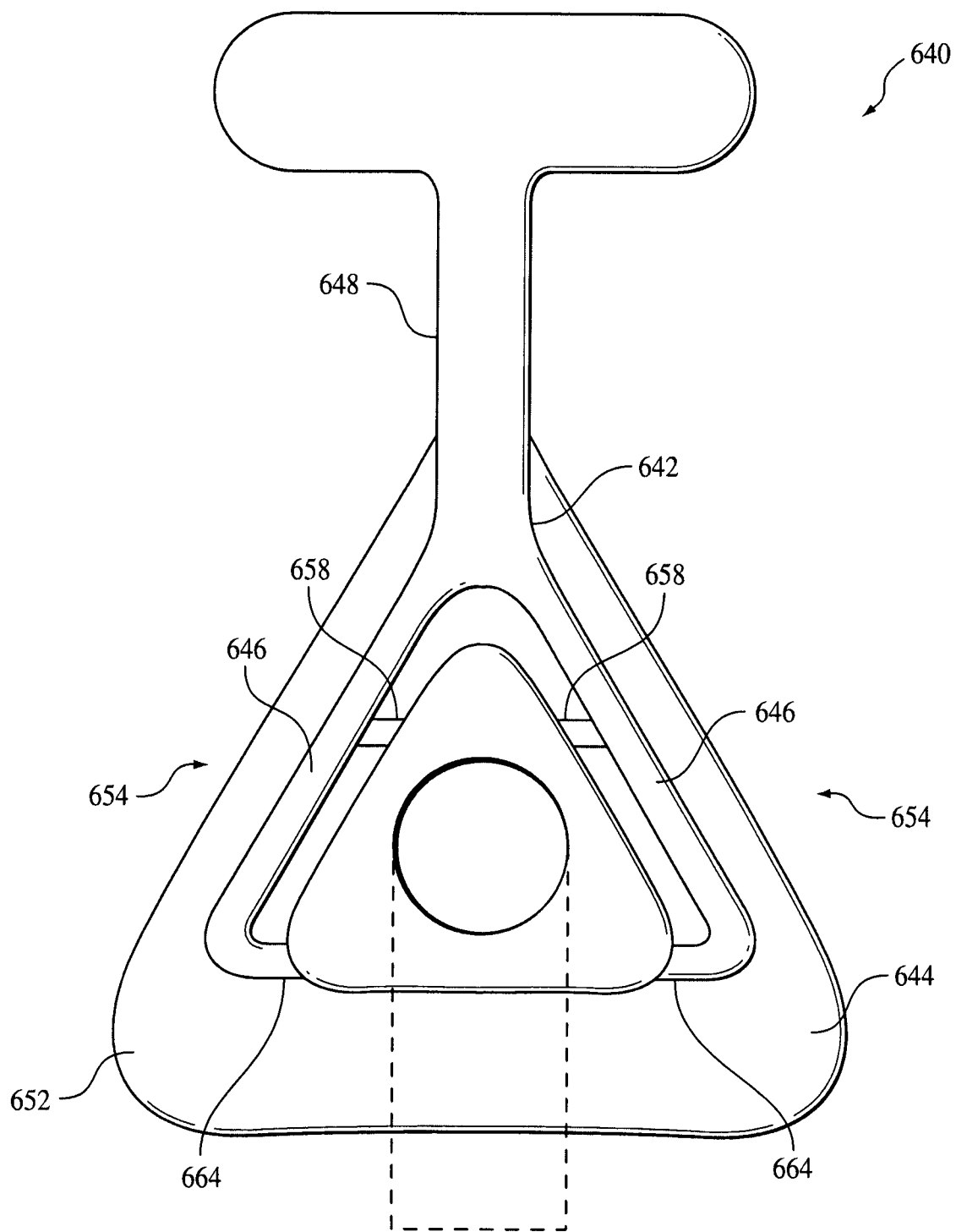
FIG. 37 is front view of a seventeenth embodiment of a patient interface according to the principles of the present invention.
Figure 38:
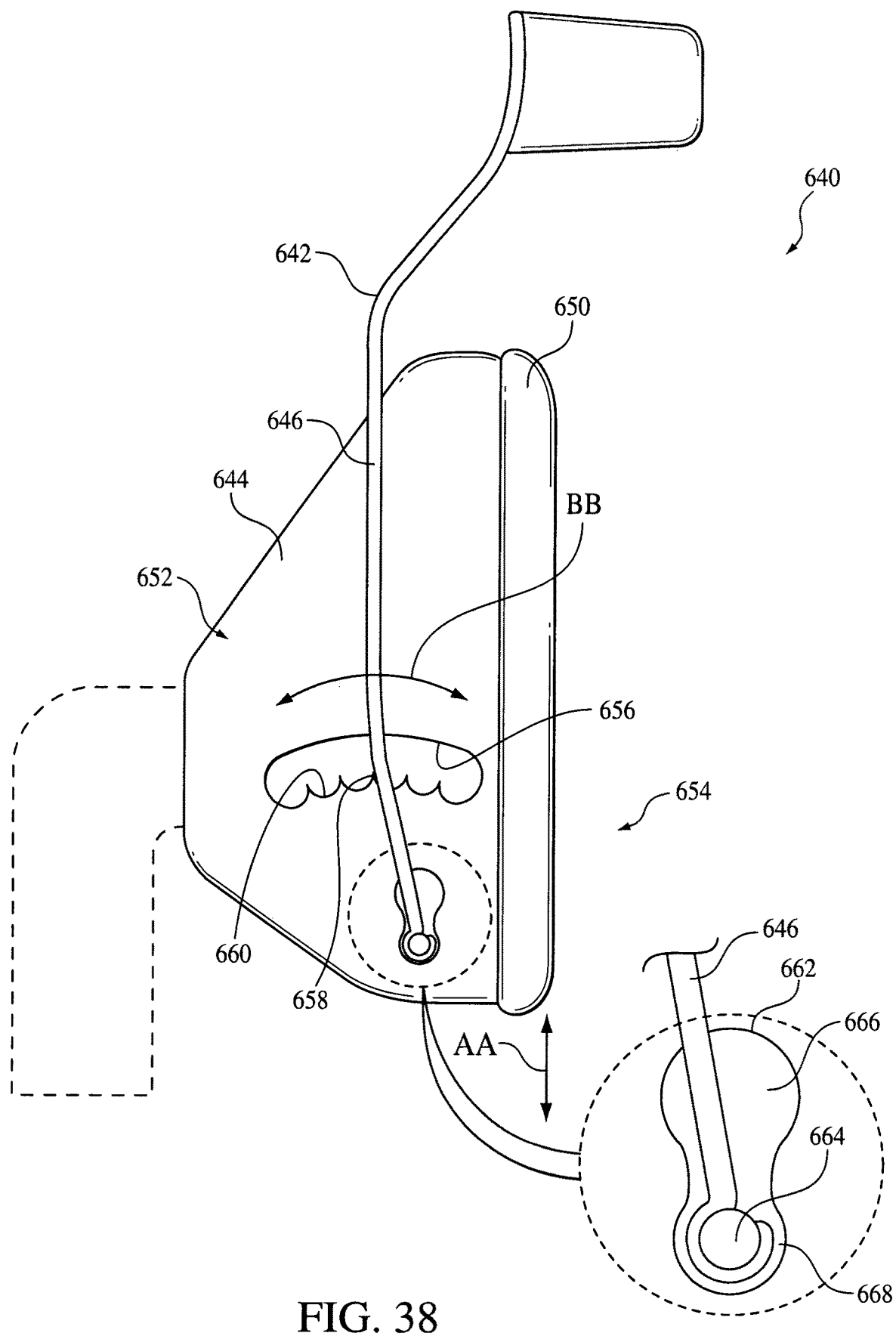
FIG. 38 is a side view the patient interface of FIG. 37 including a detailed view of an adjustment mechanism used therein.

FIGS. 37 and 38 illustrate a seventeenth embodiment of a patient interface 640 according to the principles of the present invention. Patient interface 640, which is generally similar to patient interface 610 of the previous embodiment except for the configuration for the adjustment mechanism, includes a faceplate 642 and a seal member 644. Faceplate 642 includes a pair of arms 646 and a forehead arm 648. Seal member 644 includes a cushion 650, which contacts the user, and a seal support portion 652, which supports the cushion and couples it to the faceplate.

In this embodiment, an adjustment mechanism 654 is associated with each arm 646 to allow selective angular adjustment of the seal member relative to the faceplate. Adjustment mechanism 654 includes a slot 656 provided in seal support portion 652 and a corresponding coupling member 658, which in this embodiment is a pin, that is moveable in the slot. Slot 654 also includes a plurality of notches 660 in which the coupling member sits to provide a plurality of discrete positions for the seal member relative to the faceplate. Adjustment mechanism 654 also includes a slot 662 provided at a lower portion of seal support member 658 and a corresponding coupling member 664, which in this embodiment is also a pin, that is moveable in slot 662. Slot 662 is shaped to allow the seal member to be moved relative to the seal so that coupling member 658 is disengaged from slot 654 and moved back into engagement at a desired location, as indicated by arrow AA. This is accomplished by structuring slot 662 so that it has an upper portion 666 and a lower portion 668. When disengaged, i.e., when coupling member 664, is disposed in an upper portion 666 of slot 662, the seal member is rotatable relative to faceplate 642, as indicated by arrow BB, and pin 658 slides in slot 654. Then the desired position is reached, coupling member 664 is moved into lower portion 668 of slot 662 and coupling member 658 is seated into one of the notches in slot 656.

It is to be understood that the present invention contemplates using other techniques for the adjustment mechanism in the embodiments of FIGS. 35-38. For example, a friction lock using a lock nut provided as the end of each arm can be used to lock the seal member in place with respect to the faceplate. In addition, while the threads described in the adjustment mechanisms are illustrated as being conventional threads, it is to be understood that the present invention contemplates other "non-traditional" threads, such as reverse threads and multiple spline threads.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface comprising:
   a faceplate including a plurality of headgear attachment elements, the faceplate having a seal support portion, a forehead support portion and an arm connecting the seal support portion with the forehead support portion;
   a seal member directly coupled to and extending directly from the seal support portion of the faceplate;
   a seal support member directly connected to the seal member, the seal support member being separate and distinct from the faceplate; and
   an adjustment mechanism directly connected to the seal support member and extending between the seal support member and the arm of the faceplate and coupling the seal member to the arm of the faceplate, wherein the adjustment mechanism is structured to enable movement of the seal support member relative to the faceplate such that the seal member is adjustable relative to the faceplate from a first position to a second position and structured to maintain the seal member in the second position during use of the patient interface, wherein the adjustment mechanism comprises a linkage having a first portion operatively coupled to the seal member through the seal support member and a second portion directly coupled to the arm of the faceplate, and wherein the second portion is moveable along a portion of a length of the arm of the faceplate to alter an effective length of the linkage.

2. The patient interface of claim 1, wherein the seal support member is a generally rigid annular ring disposed around the seal member.

3. The patient interface of claim 1, wherein the seal member comprises a cushion having a first end portion and a second end portion generally opposite the first end portion, wherein the first end portion includes a flexible sealing surface adapted to surround a user's nares, and wherein an opening is defined in the first end portion of the cushion for receiving a portion of said user.

4. The patient interface of claim 1, wherein the first portion of the linkage comprises an arm member and the second portion of the linkage comprises a moveable adjustment member coupled to the arm member.

5. The patient interface of claim 1, further comprising a conduit coupling member coupled to faceplate, the seal member, or both.

6. The patient interface of claim 5, further comprising an exhaust assembly disposed on the faceplate, the conduit coupling member, or both.

7. The patient interface of claim 1, wherein the seal member comprises:
   a patient contacting portion adapted to contact a surface of a patient during use of the patient interface;
   a faceplate contacting portion operatively coupled to the faceplate; and a sidewall extending between the patient contacting portion and the faceplate contacting portion.

8. The patient interface of claim 7, wherein the sidewall includes at least one bellows defined therein.

9. The patient interface of claim 1, wherein the linkage having the first portion operatively coupled to the seal member and the second portion directly coupled to the arm of the faceplate is a first linkage, wherein the adjustment mechanism further comprises a second linkage and a third linkage, wherein the first linkage, the second linkage and the third linkage are rotatably coupled together at a joint.

10. The patient interface of claim 9, wherein the second linkage has a first portion and a second portion, wherein the third linkage has a first portion and a second portion, wherein the first portion of the first linkage, the first portion of the second linkage and the first portion of the third linkage are rotatably coupled together at the joint, wherein the second portion of the second linkage is coupled to the faceplate, and wherein the second portion of the third linkage is directly connected to the seal support member.

11. The patient interface of claim 10, wherein the second portion of the second linkage is rotatably coupled to the faceplate.

12. The patient interface of claim 10, wherein the second portion of the second linkage is moveable along a portion of a length of the faceplate to alter an effective length of the second linkage.

\* \* \* \* \*